(12) United States Patent
Chen et al.

(10) Patent No.: US 9,328,172 B2
(45) Date of Patent: *May 3, 2016

(54) METHOD OF OBTAINING ANTIBODIES OF INTEREST AND NUCLEOTIDES ENCODING SAME

(75) Inventors: Chun-Nan Chen, San Jose, CA (US); James O. Bowlby, San Jose, CA (US); Richard Aleck Jorgensen, San Jose, CA (US); Mark Jay Shlomchik, Woodbridge, CT (US)

(73) Assignee: Single Cell Technology, Inc., San Jose, CA (US)

( * ) Notice: Subject to any disclaimer, the term of this patent is extended or adjusted under 35 U.S.C. 154(b) by 469 days.

This patent is subject to a terminal disclaimer.

(21) Appl. No.: 12/418,519

(22) Filed: Apr. 3, 2009

(65) Prior Publication Data

US 2011/0190148 A1    Aug. 4, 2011

Related U.S. Application Data

(60) Provisional application No. 61/072,985, filed on Apr. 5, 2008, provisional application No. 61/141,579, filed on Dec. 30, 2008.

(51) Int. Cl.
| | |
|---|---|
| C40B 30/04 | (2006.01) |
| C40B 40/06 | (2006.01) |
| G01N 33/00 | (2006.01) |
| C07K 16/40 | (2006.01) |
| C07K 16/28 | (2006.01) |

(52) U.S. Cl.
CPC ............. *C07K 16/40* (2013.01); *C07K 16/2896* (2013.01); *C07K 2317/56* (2013.01)

(58) Field of Classification Search
CPC combination set(s) only.
See application file for complete search history.

(56) References Cited

U.S. PATENT DOCUMENTS

| | | | |
|---|---|---|---|
| 4,642,284 A | 2/1987 | Cooper et al. | |
| 4,876,194 A * | 10/1989 | Bjorck et al. | ................ 435/68.1 |
| 5,110,556 A | 5/1992 | Lyman et al. | |
| 6,083,682 A | 7/2000 | Campbell et al. | |
| 6,083,683 A | 7/2000 | Pace et al. | |
| 6,087,103 A | 7/2000 | Burmer | |
| 6,091,001 A | 7/2000 | Jakobovits et al. | |
| 6,232,066 B1 | 5/2001 | Felder et al. | |
| 6,329,139 B1 | 12/2001 | Nova et al. | |
| 6,548,263 B1 | 4/2003 | Kapur et al. | |
| 6,565,813 B1 | 5/2003 | Garyantes | |
| 6,746,845 B2 | 6/2004 | Kinzler et al. | |
| 6,872,576 B1 | 3/2005 | McIntyre | |
| 7,299,134 B2 | 11/2007 | Rich et al. | |
| 7,776,553 B2 | 8/2010 | Love et al. | |
| 8,309,317 B2 * | 11/2012 | Chen et al. | ................... 435/7.92 |
| 2002/0192673 A1 | 12/2002 | Labaer et al. | |
| 2003/0022194 A1 | 1/2003 | Erlander et al. | |
| 2003/0064386 A1 | 4/2003 | Karaki et al. | |
| 2003/0124129 A1 | 7/2003 | Oliner | |
| 2004/0185439 A1 | 9/2004 | Kalush et al. | |
| 2005/0123563 A1 | 6/2005 | Doranz et al. | |
| 2005/0142539 A1 | 6/2005 | Herman | |
| 2005/0182242 A1 | 8/2005 | Snyder et al. | |
| 2006/0134704 A1 * | 6/2006 | Muraguchi et al. | ............ 435/7.2 |
| 2006/0177868 A1 | 8/2006 | Okamoto et al. | |
| 2006/0223194 A1 * | 10/2006 | Lopez-Avila et al. | ........ 436/514 |
| 2006/0269969 A1 | 11/2006 | Angelides | |
| 2007/0148690 A1 | 6/2007 | Shao et al. | |
| 2007/0161009 A1 | 7/2007 | Kohne | |
| 2007/0238089 A1 | 10/2007 | Rosenthal et al. | |
| 2008/0004185 A1 | 1/2008 | Labgold | |
| 2008/0090239 A1 | 4/2008 | Shoemaker et al. | |
| 2009/0088336 A1 | 4/2009 | Burd et al. | |
| 2009/0117555 A1 | 5/2009 | Kuypers et al. | |
| 2010/0035763 A1 | 2/2010 | Chen et al. | |

FOREIGN PATENT DOCUMENTS

WO    WO 20071076580    7/2007

* cited by examiner

*Primary Examiner* — Catherine S Hibbert
*Assistant Examiner* — Channing S Mahatan
(74) *Attorney, Agent, or Firm* — Convergent Law Group LLP

(57) ABSTRACT

The invention is a methodology which makes it possible to select from a very large number of cells, a single cell or cells of interest and obtain specific information from those cells in a rapid and efficient manner. As an example of the methodology, a large number of antibody producing cells such as plasma cells are separated so that these individual antibody producing plasma cells are placed in individual wells. The cells are allowed to produce antibodies and the antibodies in the wells are then contacted with a protein bound to a solid surface such as a well top. The protein universally and specifically binds antibodies in the wells. The surface or well tray top includes addresses configured such that each address is specifically related to one of the individual wells containing a cell producing antibodies.

19 Claims, 10 Drawing Sheets

Mouse heavy chain oligonucleotide probe (SEQ ID NO:1)

Mouse light chain oligonucleotide probe (SEQ ID NO:2)

METHOD OF OBTAINING ANTIBODIES OF INTEREST AND NUCLEOTIDES ENCODING SAME

CROSS-REFERENCE

This application claims the benefit of U.S. Provisional Application Nos. 61/072,985, filed Apr. 5, 2008 and 61/141,579, filed Dec. 30, 2008, which applications are incorporated herein by reference. This application is related to two other applications filed concurrently herewith on Apr. 3, 2009 which two related applications are incorporated herein by reference in their entirety.

FIELD OF THE INVENTION

This invention generally relates to a method of isolating from a large number of cells, a cell producing an antibody of interest. More particularly, the invention relates to indentifying antibodies of interest being produced by a cell and determining the sequence which encodes the antibody.

BACKGROUND OF THE INVENTION

Molecular interactions are critical for maintaining cellular functions. These interactions can be classified into 3 broad categories. The first is protein complex formation via covalent bonds such as the heavy chain and light chain of an immunoglobulin. The second is protein-protein association via non-covalent bonds exemplified by heterodimer formation of HER-2 and EGFR (epidermal growth factor receptor). The third is an association between 2 molecules involved in a cellular pathway such as a cytokine receptor and a caspase in an apoptosis pathway.

Antigen binding proteins involved in the immune response are present in mammals as large polyclonal repertoires representing a broad diversity of binding specificities. This diversity is generated by rearrangement of gene sequences encoding variable regions of these binding proteins. Such variable region binding proteins include soluble and membrane-bound forms of the B cell receptor (also known as immunoglobulins or antibodies) and the membrane-bound T cell receptors (TCR). With respect to immunoglobulins, their affinity is enhanced subsequent to recognition of an antigen by a B cell antigen receptor, through a process termed affinity maturation which involves cycles of somatic hypermutation of these variable genes.

Known approaches for isolating antibodies with a desired binding specificity most often either involves generation of hybridoma cells from immunized hosts followed by screening for specific clones or involves the generation of combinatorial expression libraries in $E.\ coli$ composed of immunoglobulin variable domains, which are subsequently screened using techniques such as phage display.

There are several limitations in the use of the hybridoma technology. The generation time for a specific hybridoma can be long (5-15 months). Functional screens are possible only after clone selection and culture. Furthermore, if a hybridoma is desired for producing human antibodies, typically for therapeutic purposes, then alternative strategies must be sought because of the absence of human myeloma lines suitable as fusion partners for human B lymphocytes. Heterohybridomas, i.e., fusion of human B cells with mouse myeloma cells, were attempted but they are extremely unstable and thus rarely lead to suitable cell lines for production purposes. Human B cells immortalized through infection with Epstein-Barr virus exhibit similar instability.

Use of combinatorial libraries and phage display allows for generation of large repertoires of antibody clones with a potential diversity in excess of $10^{10}$. From this repertoire, selection for binding to a specific target can be performed thereby generating a sub-library. This sub-library can be used to generate either polyclonal or monoclonal antibodies. The variable region encoding sequences (for example heavy chain variable region and light chain variable region encoding sequences) which are to constitute the library can be amplified from lymphocytes, plasma cells, hybridomas or any other immunoglobulin expressing population of cells. Current technologies for generating combinatorial libraries involve separate isolation of the variable region encoding sequences. Thus, the original pairing of, for example, immunoglobulin heavy chain variable region and light chain variable region encoding sequences is lost. Said sequences are randomly paired and the original combinations of these variable sequences only occur by chance.

Thus, in order to isolate variable region encoding sequences responsible for a desired binding specificity, a considerable amount of screening is necessary. This is typically performed in combination with methods for enrichment of clones exhibiting a desired specificity, such as ribosome display or phage display. Even then, the diversity achieved might not be sufficiently large to isolate variable region encoding sequence pairs giving rise to binding proteins of similar high affinity as those found in the original cells. Further, the enrichment procedures normally used to screen combinatorial libraries introduce a strong bias, e.g. polypeptides of particular low toxicity in $E.\ coli$, efficient folding, slow off-rates, or other system dependent parameters, thus reducing the diversity of the library even further. In addition, clones derived from such combinatorial libraries will be more prone to producing binding proteins with cross reactivity against self-antigens because they, in contrast to original pairs (hereafter called cognate pairs), have never been subjected to in vivo negative selection against self-antigens as pairs, such as is the case for B- and T-lymphocyte receptors during particular stages of their development. Therefore, the identification of cognate pairs of variable region encoding sequences is a desirable approach. Moreover, the frequency of clones exhibiting a desired binding specificity is expected to be considerably higher within a library of cognate pairs than in a conventional combinatorial library, particularly if the starting cells are derived from a donor with high frequency of cells encoding specific binding pairs, e.g., immune or immunized donors.

In order to generate cognate pair libraries the linkage of the variable region encoding sequences derived from the same cell is required. At present, 3 different approaches that achieve cognate pairing of variable region encoding sequences have been described.

In-cell PCR is an approach where a population of cells is fixed and permeabilized, followed by in-cell linkage of heavy chain variable region and light chain variable region encoding sequences from immunoglobulins. This linkage can be performed either by overlap extension RT-PCR or by recombination. The amplification process, as described in these publications, is a three to four step process consisting of i) reverse transcription utilizing constant region primers generating immunoglobulin cDNA, ii) PCR amplification of the heavy and light chain variable region encoding sequences utilizing primer sets containing either overlap-extension design or recombination sites, iii) optional linkage by recombination, and iv) nested PCR of the products generating restriction sites for cloning. Since the cells are permeabilized there is a considerable risk that amplification products might leak out of the cells, thereby introducing scrambling of the heavy chain variable region and light chain variable region encoding sequences, resulting in the loss of cognate pairing. Therefore, the procedure includes washing steps after each reaction which makes the process laborious and reduces the efficiency of the reactions.

More generally, the in-cell PCR is extremely inefficient, resulting in low sensitivity. Accordingly, the in-cell PCR linkage technique has never found widespread usage, and the original studies have never been reliably repeated in a way that can verify that the linkage actually occurs within the cell. This, however, is absolutely crucial to avoid scrambling the heavy chain variable region and light chain variable region encoding sequences and thereby disrupting the cognate pairs.

Single-cell PCR is a different approach to achieve cognate pairing of heavy chain variable region and light chain variable region encoding. In these publications, a population of immunoglobulin expressing cells are distributed by diluting to a density of one cell per reaction, thereby eliminating scrambling of heavy chain variable region and light chain variable region encoding sequences during the cloning process. The process described is a three to four step procedure consisting of i) reverse transcription utilizing oligo-dT-, random hexamer- or constant region primers generating cDNA, ii) fractionating the cDNA product into several tubes and performing PCR amplification on the individual variable chain encoding sequences (in separate tubes) with primer sets containing restriction sites for cloning, iii) nested PCR of the products generating restriction sites for cloning (optional) and iv) linking the heavy chain variable region and light chain variable region encoding sequences from the separate tubes by cloning them into an appropriate vector, which is itself a multi-step process.

In humans, there are two types of light chains: lambda ($\lambda$) and kappa ($\kappa$). This means that with the cDNA generated from every single cell at least three separate PCR reactions must be performed followed by analysis and cloning of the appropriate bands into a single vector to achieve cognate pairing. Thus, the single-cell PCR approach as described requires a large number of reactions to generate a library of cognate pairs. Although, a cognate pair library does not need to be as large as a combinatorial library in order to obtain binding proteins representing a broad diversity of binding specificities it would still be a laborious task to generate a library of, for example, $10^4$ to $10^5$ clones by the described single cell PCR approach. Further, the large number of steps greatly increases the risk of contamination and human error.

Symphogen's (Symphogen A/S, Lyngby, Denmark) approach is to use multiplex overlap-extension RT-PCR (reverse transcription-polymerase chain reaction) to identify the natural pairing of heavy chain and light chain antibodies by isolating single B cells in a well of a 96-well microtiter plate. However, the process is labor intensive and verification of the structure of individual antibodies is inefficient since each pair needs to be tested separately by expressing the corresponding single chain Fv in *E. coli*.

PCR primer based DNA barcoding has been described in the literature. There have been studies utilizing oligonucleotide tags to label DNA molecules during sample preparation such that after sequencing by a massively parallel technology, one is able to digitally sort DNA sequences originating from different samples or a positive control. However, each tagging PCR primer must be individually synthesized. As such, when a large number of samples are processed, this practice will become prohibitively expensive. Consequently, the technique is only suitable for a limited number of samples.

SUMMARY OF THE INVENTION

The invention is a methodology which makes it possible to select from a very large number of cells, a single cell or cells of interest and obtain specific information from those cells in a rapid and efficient manner. As an example of the methodology, a large number of antibody producing cells such as plasma cells are separated so that these individual antibody producing plasma cells are placed in individual wells. The cells are allowed to produce antibodies and the antibodies in the wells are then contacted with a protein bound to a solid surface such as a well top. The protein universally and specifically binds antibodies in the wells. The surface or well tray top includes addresses configured such that each address is specifically related to one of the individual wells containing a cell producing antibodies.

Information relating to the antibodies which bind the protein on the surface is then obtained. The information can be the binding affinity of the antibodies at a particular address for a particular known antigen. The information at all of the addresses may be analyzed or screened simultaneously in order to find the address or particular group of addresses which are of particular interest such as antibodies with a high binding affinity to the particular known antigen. The screening of the antibodies can be done by contacting the antibodies with antigens of interest which antigens may be labeled. After identifying the addresses of the antibodies of interest those addresses are correlated to the well or wells of interest.

Information relating to the DNA sequence of the antibodies is then obtained and correlated with said antibodies of interest. This is done by lysing the antibody and then isolating mRNA encoding the antibodies of interest.

After isolating mRNA the mRNA is used to produce cDNA. The cDNA may be sequenced and the cDNA may be used to genetically engineer cells which produce antibodies of interest. The cDNA may be synthesized to incorporate specific tags that correlate to the physical location of wells, the physical location of antibodies on the surface, and the DNA sequence. The specific tags allow the pooling of cDNA from all wells for subsequent determination of the individual cDNA sequences. The sequences of particular interest are those encoding the light and heavy chain variable regions or portions thereof sufficiently large to construct an antibody of interest. The sequences of the light and heavy chain of each antibody are associated using the specific tags.

The methodology can be used with hundreds, thousands, tens of thousands, hundreds of thousands, millions or more cells at the same time. By using this technique it is possible to sort through large numbers of cells quickly and identify those cells which produce antibodies of interest and relate those antibodies directly to the nucleotide sequence responsible for producing the antibodies desired.

The present invention provides an efficient method for analyzing a large number of cells. The present invention solves the problem of reporting the average measurement for a population of cells. In one embodiment cells are separated and processed in small microwells where diffusion of molecules among microwells is retarded or blocked. On the other hand, each microwell, due to its small dimensions, facilitates rapid reaction rates, such as mRNA hybridization or capture of proteins. After disruption of each cell, mRNAs from target genes are captured by oligonucleotide probes located inside each microwell. Simultaneously, corresponding protein(s) or protein complexes are retained by a capture agent confined to each microwell. Conversion of the captured mRNA into double-stranded cDNA incorporates an oligonucleotide tag unique to each microwell. The cDNA can then be pooled and sequenced by ultra-high throughput DNA sequencing technology to determine the structure of each member of the protein complex in each originating cell. The captured proteins form an array on a substrate where their kinetic properties can be analyzed when contacting with labeled affinity ligands common to all captured proteins or complexes. Such measured kinetic properties can be used to a) rank the protein complexes with respect to affinity b) filter DNA sequence data thereby removing contaminating or irrelevant cells from consideration, c) classify the type of cell based on the quantity of protein complex, or d) measure the frequency of cells producing similar protein complexes. Thus, by measuring the frequency at which cells produce a particular protein such as an antibody it is possible to determine various characteristics regarding antibodies which might be produced in response to a particular antigen and also determine additional information which may be useful in characterizing desirable antibodies.

In one of the embodiments, the protein complex under study can be the heavy chain and light chain of an antibody. In this case, integrating structural information with kinetic properties provides insights into the paratopes on the antibody as well as the epitopes on the antigen. To illustrate this utility of the present invention, simulation with antibodies against the hapten 2-phenyl-5-oxazolone (phOX) was performed.

The present invention has many potential uses but a major application is likely to be the analysis of gene combinations that are polymorphic within a population of cells, such as the rearranged genes for Ig or T cell receptors or secreted antibodies.

The present invention provides a method for characterizing molecular interactions within a single cell. This is accomplished by determining the structure of cis- and/or trans-protein complexes and optionally measuring binding kinetic properties between said cis- and/or trans-protein complexes and a ligand. The invention separates a plurality of cells into a plurality of microwells wherein the ratio of the number of microwells containing 2 or more cells divided by the number of microwells containing a single cell is less than 20%. Said microwells possess the following properties: a) each microwell has a volume between 1 picoliter and 500 nanoliters; b) said microwells occupy a density greater than 100 wells per $cm^2$; c) said microwells are intermittently accessible to external reagents; d) oligonucleotides are attached to surfaces inside said microwells; e) said oligonucleotides contain less than 100 sequences complementary to mRNA coding for said cis- and/or trans-protein complexes; and f) said oligonucleotides contain one or more unique tags common to all identical oligonucleotides within the same microwell. The invention further comprises lysing said cells, optionally capturing said cis- and/or trans-protein complexes on surfaces inside said microwells, subjecting said cis- and/or trans-protein complexes to differing concentrations of fluorescently labeled ligands, and measuring the decrease in fluorescence over time, capturing said mRNA by hybridizing them to said oligonucleotides, converting said captured mRNA to cDNA, pooling said cDNA and sequencing them, and digitally reconstructing said structure of said cis- and/or trans-protein complexes from the cDNA sequences associate with each cell.

These and other objects, advantages, and features of the invention will become apparent to those persons skilled in the art upon reading the details of the methods and embodiments of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DEFINITIONS

Figure 1:
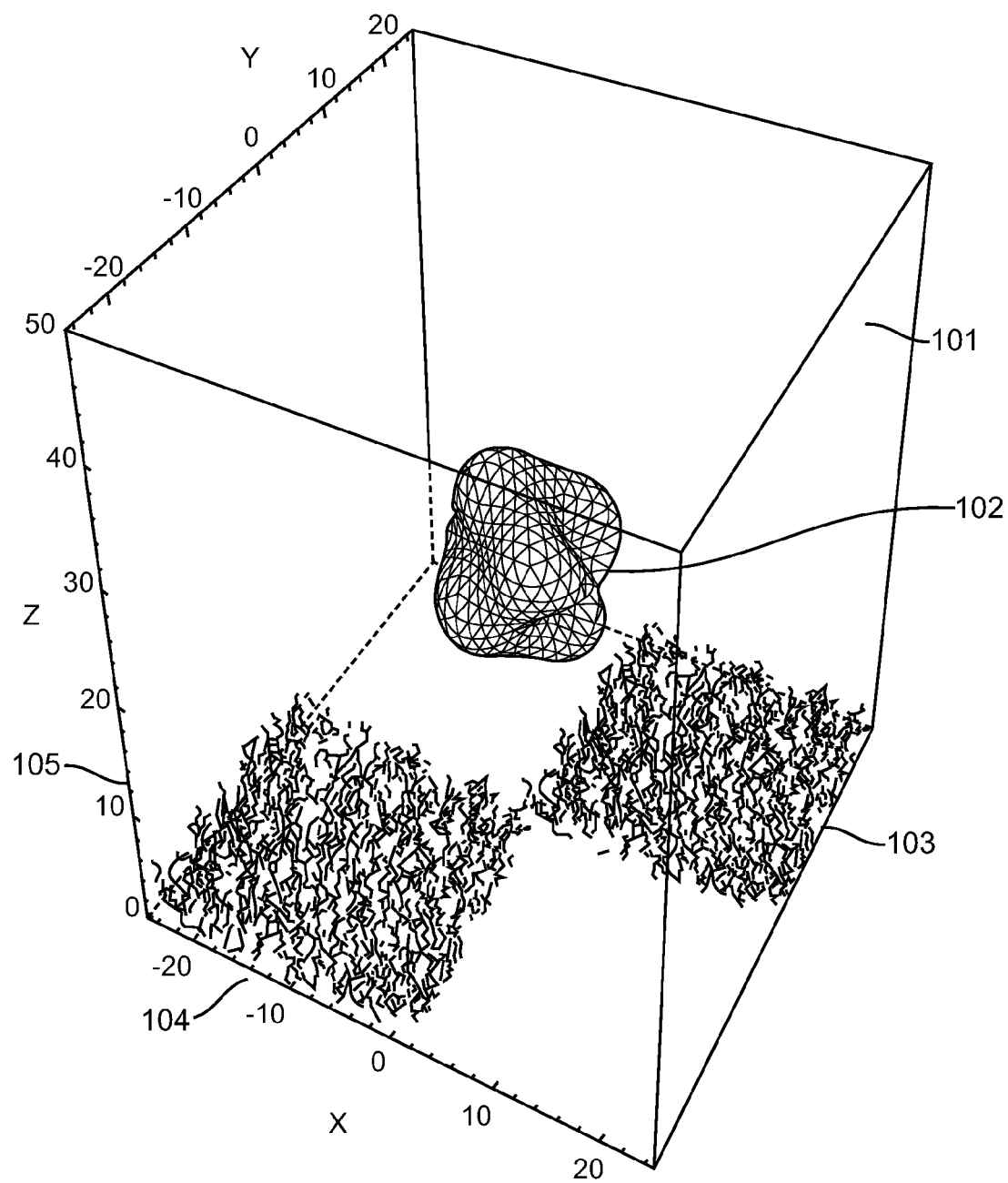
FIG. 1 is a schematic representation of a B cell or plasma cell captured in a micro-well.

As used herein, the terms "tag(s)" or, "oligonucleotide tag(s)" refer to an oligonucleotide whose sequence identifies the physical location of its origin.

The term "oligonucleotide" as used herein includes linear oligomers of natural or modified monomers or linkages, including deoxyribonucleosides, ribonucleosides, anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3-4, to several tens of monomeric units, e.g. 40-60. Whenever an oligonucleotide is represented by a sequence of letters, such as "ATGCCTG," it will be understood that the nucleotides are in 5'.-0.3° order from left to right and that "A" denotes deoxyadenosine, "C" denotes deoxycytidine, "G" denotes deoxyguanosine, and "T" denotes thymidine, unless otherwise noted. Usually oligonucleotides of the invention comprise the four natural nucleotides; however, they may also comprise non-natural nucleotide analogs. It is clear to those skilled in the art when oligonucleotides having natural or non-natural nucleotides may be employed, e.g. where processing by enzymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews 90:543-584 (1990), or the like, with the only proviso that they are capable of specific hybridization. Such analogs include synthetic nucleosides designed to enhance binding properties, reduce complexity, increase specificity, and the like.

As used herein "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identification, ordering, and locations of one, two, or three of the four types of nucleotides within a target polynucleotide.

As used herein, "epitope" is the part of a macromolecule that is recognized by the immune system, specifically by antibodies, B cells, or T cells. Although epitopes are usually thought to be derived from nonself proteins, sequences derived from the host that can be recognized are also classified as epitopes. Most epitopes recognized by antibodies or B cells can be thought of as three-dimensional surface features of an antigen molecule; these features fit precisely and thus bind to antibodies.

As used herein, "hybridization" refers to the process wherein cellular RNA or single stranded DNA interacts with oligonucleotides having substantial sequence complementarity, wherein duplexes are formed in said regions of sequence complementarity.

As used herein, "microwell" refers to sub millimeter structures with a volume between 1 picoliter and 500 nanoliters. The microwell is typically constructed in a shape that allows dense packing on a planar substrate, i.e.: the shape is triangular, rectangular, or hexagonal. Microwells can be either opened by removing one surface, usually at the top, or closed by placing said top in contact with other surfaces. The microwell can be homogeneous, or constructed out of dissimilar materials, including but not limited to glass, photoresist, or polydimethylsiloxane (PDMS).

As used herein, "paratope" refers to the part of an antibody that recognizes the epitope of an antigen.

As used herein, "phOX" refers to 4-{[(Z)-(5-OXO-2-PHE-NYL-1,3-OXAZOL-4(5H)-YLIDENE)METHYL] AMINO}BUTANOIC ACID, represented by the chemical formula $C_{14}H_{12}N_2O_4$ As used herein, "rotamers" refer to low energy side-chain conformations. The use of a build-library of rotamers allows anyone determining or modeling a structure to try the most likely side-chain conformations, saving time and producing a structure that is more likely to be correct. This is, of course, only the case if the rotamers really are the correct low energy conformations. Libraries address this quality issue in a number of ways: they use only very high resolution structures (1.8 Å or better), remove side chains whose position may be in doubt using a number of filters, use the mode rather than the mean of observed conformations (which has a number of advantages), and make efforts to remove systematically misfit conformations.

As used herein, "mutations" are changes to the nucleotide sequence of the genetic material of an organism. Mutations can be caused by copying errors in the genetic material during cell division, by exposure to ultraviolet or ionizing radiation, chemical mutagens, or viruses, or can occur deliberately under cellular control during processes such as hypermutation. In multicellular organisms, mutations can be subdivided into germ line mutations, which can be passed on to descendants, and, as used herein, "somatic mutations", which cannot be transmitted to descendants in animals. B cells undergo somatic mutations during the process of affinity maturation.

To be able to perform their biological function, proteins fold into one, or more, specific spatial conformations, driven by a number of noncovalent interactions such as hydrogen bonding, ionic interactions, Van der Waals' forces and hydrophobic packing. As used herein, "structure" refers to four distinct aspects of a protein's structure: a) the primary structure is the amino acid sequence of the peptide chains, b) the secondary structure is the highly regular sub-structures (alpha helix and strands of beta sheet) which are locally defined, meaning that there can be many different secondary motifs present in one single protein molecule, c) tertiary structure is the three-dimensional structure of a single protein molecule; a spatial arrangement of the secondary structures, and d) the quaternary structure is the complex of several protein molecules or polypeptide chains, usually called protein subunits in this context, which function as part of the larger assembly or protein complex.

As used herein, "capture agent" is a molecule used to immobilize a cis protein complex. Capture agents can be oligonucleotides, DNA, RNA, protein, small molecules, peptides, aptamers, etc which have an affinity for their respective natural or artificial ligands.

The term "monoclonal antibody" relates to an antibody chosen from a mixture of different antibodies. All monoclonal antibodies of the same specificity are identical except for natural mutants thereof. Under the term "antibody" intact molecules of immunoglobulins as well as fragments thereof (Fab, F(ab'), Fv, scFv) are to be understood.

As used herein, a "ligand" is a substance that is able to bind to and form a complex with a biomolecule to serve a biological purpose.

The term "B cell" is used herein to mean an immune cell that develops in the bone marrow and is highly specialized for making immunoglobins and antibodies. A B cell is a lymphocyte which is derived from bone marrow and provides humoral immunity. A B cell recognizes antigen molecules in solution and matures into a plasma cell. Thus, when the term "B cell" is used herein it is intended to encompass cells developed from B cells such as plasma cells.

The term "plasma cell" is intended to mean a cell that develops from a B lymphocyte in reaction to a specific antigen. Plasma cells are found in bone marrow and blood. A plasma cell may also be called a plasma B cell or plasmacyte and are cells in the immune system which secrete large amounts of antibodies. Plasma cells differentiate from B cells upon stimulation by CD4+ lymphocytes. A plasma cell is a type of white blood cell that produces antibodies and is derived from an antigen-specific B cell. Throughout this application the term "B cell" is intended to encompass "plasma cells" and vice versa. In general both are intended to encompass terms referring to cells which produce antibodies of interest.

In the field of immunology, antibodies are characterized by their "binding affinity" to a given binding site or epitope. Every antibody is comprised of a particular 3-dimensional structure of amino acids, which binds to another structure referred to as an epitope or antigen.

The binding of an antibody to its antigen is a simple bimolecular, reversible reaction. If the antibody is represented by Ab and the antigen by Ag, the reaction can be analyzed by standard kinetic theory. Assuming a single binding site the reaction is represented by the equation I as follows:

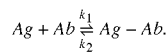  I where Ag–Ab is the bound complex. The forward and reverse binding reactions are represented by rate constants k1 and k2 respectively. The "binding affinity" of the antibody to the antigen is measured by the ratio of complexed to free reactants at equilibrium. The lower the concentration of the reactants at equilibrium, the higher the binding affinity of the antibody for the antigen. In the field of immunology, the binding affinity is represented by an "affinity constant" which is represented by the symbol "K" or sometimes referred to as "Ka". The "K" is defined by the equation II as follows:

$$K = \frac{[Ag - Ab]}{[Ag][Ab]} = \frac{k_1}{k_2}.$$  II where the brackets denote concentration in moles per liter or liters per mole.

A typical value for the binding affinity Ka which is also referred to as "K" and is the "affinity constant" which for a typical antibody is in a range of from about $10^5$ to about $10^{11}$ liters per mole. The Ka is the concentration of free antigen needed to fill half the binding sites of the antibody present in solution with the antigen. If measured in liters per mole a higher Ka (e.g. $10^{11}$) or higher affinity constant indicates a large volume of solvent, a very dilute concentration of free antigen, and as such indicates the antibody has a high binding affinity for the epitope.

If the Ka is measured in moles per liter a low Ka (e.g. $10^{-11}$) indicates a less concentrated solution of the free antigen needed to occupy half of the antibody binding sites, and as such a high binding affinity.

Equilibrium is achieved in order to measure the Ka. More specifically, the Ka is measured when the concentration of antibody bound to antigen [Ag–Ab] is equal to the concentration of the antibody [Ab]. Thus, [Ag–Ab] divided by [Ab] is equal to one. Knowing this, the equation II above can be resolved to the equation III as follows:

$$K = \frac{1}{[Ag]}.$$  III

In equation III the units for K are liters per mole. Typical values in liters per mole are in a range of from about $10^5$ to about $10^{11}$ liters per mole.

The inverse of the above equation is K=[Ag] where the units for K are in moles per liter, and the typical values are in a range of $10^{-11}$ to $10^{-5}$ moles per liter.

The above shows that typical binding affinities can vary over six orders of magnitude. Thus, what might be considered a useful antibody might have 100,000 times greater binding affinity as compared to the binding affinity of what might be considered a different antibody, which is also considered useful.

Based on the above it will be understood that binding characteristics of an antibody to an antigen can be defined using terminology and methods well defined in the field of immunology. The binding affinity or "K" of an antibody can be precisely determined.

The term "protein complex" is used to refer to a group of two or more constituent proteins formed by protein-protein interactions that may or may not involve formation of covalent bonds. Protein complexes are a form of quaternary structure. An example is IgG, which is formed by a heavy chain and a light chain. In this case, there are disulfide linkages between the heavy and light chains. Protein complexes that are formed by constituent proteins deriving from the same cell are referred to as "cis protein complexes". As such, IgG is a perfect example of a cis protein complex. In contrast, protein complexes that are formed by constituent proteins deriving from different cells or different origins are referred to as "trans protein complexes." An example of a trans protein complex is an antibody-antigen complex. Interestingly, an antibody-antigen complex involves a nested cis protein complex. The present invention relates to both cis and trans protein complexes.

As used herein, "kinetic properties" refer to the rates of reaction $k_{off}$, $k_{on}$, and their ratio $K_D$ between cis and/or trans protein complexes. For a binary protein complex, the dissociation constant $K_D$ is monotonically related to the Gibbs free energy which describes the work obtainable from an isothermal, isobaric process, conditions closely approximated in living systems.

Those skilled in the art will understand that a high degree of binding affinity does not necessarily translate to a highly effective drug. Thus, when obtaining drug candidates the candidates showing a wide range of binding affinities may be tested to determine if they obtain the desired biochemical/physiological response. Although binding affinity is important, some drug candidates with high binding affinity are not effective drugs and some drug candidates with low binding affinity are effective drugs.

DETAILED DESCRIPTION OF THE INVENTION

Before the present methods and devices for efficiently obtaining information from large numbers of cells are described, it is to be understood that this invention is not limited to particular methods and devices described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell or sequence" may include a plurality of such cells or sequences and reference to "the well or addresses" may include reference to one or more wells or addresses and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Specific Embodiments

The present invention provides a method for characterizing molecular interactions within a single cell. Central to said method is the confinement of single cells into individual addressable microwells. Said microwells serve 2 purposes. One is to inhibit the diffusion of reactants and products among individual cells. Second is to accelerate rates for processes such as nucleic acid hybridization or protein interactions. Moreover, said microwell comprises capture agents that allow efficient capture of the intended macromolecules on a cell by cell basis.

Inside each microwell, one or a plurality of capture agents each comprise a tag unique to the addressable microwell where a single cell is confined. When a cell is confined and disrupted, the target macromolecules can be captured rapidly. Subsequent to capture, the means for confinement may optionally be removed to allow manipulation of the captured macromolecules and/or measurement of kinetic properties of the interactions between the captured macromolecules and a labeled ligand. The captured macromolecules such as mRNA can be converted into double stranded (ds) cDNA incorporating said tag identifying its originating microwell. Said ds cDNA can then be aggregated and processed by massively parallel single-molecule based DNA sequencing technology. During the sequencing process, said microwell identifying tags are converted into digital tags in the form of a DNA sequence. Said digital tags can then be used to identify and cluster the primary structure of the distinct constituent macromolecules as part of a cis or trans protein complex originating from a single cell.

When fluorescent measurements are taken, of cells or surface bound antibodies, a microarray reader produces an image wherein the intensity of various pixels must be associated with the concentration of cell surface markers, or surface bound antibodies, in specific wells. To insure proper registration between the confined cell, the captured mRNA, and optionally the captured protein, it is desirable to include marker cells with a known cis protein complex into the cell population under investigation.

The system can be tested using a hybridoma cell line that is optionally capable of expressing membrane bound antibody with known sequence information for both heavy and light chain. Such lines are deposited and described in the literature and easily acquired. These cells can be stained with an antigen labeled with a distinct fluorophore so they can be identified in the addressable microwells. In addition, their respective mRNA will be processed and sequenced so the DNA sequence plus the digital tags will positively identify the position of the marker cells on the capture microarray slide. On the other hand, the antibody captured on the array can also be stained with the appropriate antigen with the distinct dye to identify its position on the protein array. As such, the position of the marker cells on the microarray slide can be matched with those on the protein array. The mRNA and protein of other cells in the array can be matched based on their position relative to the marker cells, their mRNA and antibodies.

One embodiment of the method of the invention comprises a method of obtaining information from a plurality of isolated cells. The information may be simultaneously obtained from a large number of cells by placing the large number of cells in individual wells. An attempt is made to include a single cell within a single well. However, when carrying out the method involving hundreds, thousands or even tens of thousands of cells and wells it may be that some wells do not include a cell and other wells include more than one cell.

A method of the present invention may begin with immunizing an animal and extracting antibody producing cells from that animal. However, the process may begin with the cells already having been extracted and placing the cells into wells of a well tray. Those skilled in the art will recognize that the methodology of the invention can be carried out in a variety of different ways. In one embodiment a well tray comprised of microwells is used. The microwells have a volume sufficient to accommodate a single cell and liquid nutrient to support the cell for a limited period of time during which the cell produces antibodies. Those skilled in the art will recognize that it is desirable to place a single cell within each microwell. However, when the process is actually carried out some wells will not contain a cell and some wells may contain two or more cells. Although this can limit the effectiveness of the invention, the invention can be carried out when only a small percentage of the microwells contain a single cell, e.g. 1%, 5%, 10%, 50% or more of the cells only contain a single cell and the remainder of the wells contain no cell or a plurality of cells, i.e. 2 or more cells. It is desirable if a very high percentage, 70% or more, 80% or more, 90% or more, or 95% or more of the wells contain a single cell and only a single cell. This makes it possible to utilize all of the wells and specifically relate antibodies produced in the well to a single cell. Those skilled in the art will also recognize that even though it is desirable that all of the cells produce antibodies some of the cells may not produce antibodies or may produce antibodies in insufficient amounts to be detectable. The invention that can be carried out when a relatively small number of the cells are actually producing antibodies. For example, it may be that only 1%, 5%, 10% or 50% of the cells in the wells are actually producing antibodies in detectable amounts even though it is desirable to obtain a high percentage of antibody producing cells, e.g. 70% or more, 80% or more, 90% or more, or 95% or more of the cells placed in wells are producing antibodies. The more wells containing a single cell which is producing antibodies the greater the efficiency of the methodology of the invention.

The cells are cells such as B cells or plasma cells which produce antibodies and the antibodies which are produced in the wells are brought into contact with a binding agent such as protein A which is bound to a surface which may be a membrane. This surface may have a plurality of addressable regions or will include regions which can be specifically relatable to individual wells. The wells may be in a well tray which has a well density of 100 or more wells per cm² or 1,000 or more wells per cm² and the wells may include a detectable marker which makes it possible to determine the position of a particular well relative to other wells and the marker may be a marker cell or a group of markers which could include a dye, a nucleotide sequence, a radioactive label or a quantum dot.

After contacting antibodies in the wells with the binding agent a process is carried out to determine binding information relating to the binding of the antibodies which are bound to the surface to an antigen which is preferably a specific known antigen in order to determine information such as the binding affinity of the antibodies to that antigen. The binding information relating to specific areas on the surface is then associated with the particular well in which the antibodies were obtained. Thus, it is possible to simultaneously obtain information from a large number of different wells relating to a large number of different antibodies and associate the antibodies with the wells from which the antibodies were obtained.

After determining particular antibodies on the areas of the surface which are of interest and associating those with the wells of interest it is possible to obtain specific polynucleotide information from the particular wells which information is generally sequence information regarding messenger RNA obtained from particular wells of interest. The messenger RNA may be obtained by binding messenger RNA in the wells to sequences which selectively bind to sequences which encode antibodies such as sequences which encode light and heavy chains of antibodies.

The messenger RNA obtained can be converted to cDNA. The cDNA may contain tags which are specific to the well of particular interest. The tag may be used to associate binding information relating to antibodies of particular interest with messenger RNA from wells of particular interest. The invention is described in further detail below with reference to the figures.

Microwell 101 of FIG. 1 may have dimensions 50 microns by 50 microns by 50 microns. Dimensions 105 measure 0 to 50 microns from the bottom of microwell 101 to the top. From one side to the opposite side the dimensions range from −25 microns to 25 microns. A plasmocyte 102 is suspended inside microwell 101 in a buffered solution that fills the entire microwell. DNA oligonucleotides are attached to the bottom surface of microwell 101 in contiguous areas called pads. Pad 103 contains an oligonucleotide complementary to an invariant sequence in the mRNA of plasmocyte 102 that codes for the heavy chain of an antibody. Pad 104 contains an oligonucleotide complementary to an invariant sequence in the mRNA of plasmocyte 102 that codes for the light chain of an antibody. Said invariant sequences are selected so they will bind strongly and physically capture complementary mRNA when said mRNA is released from plasmocyte 102 and diffuses into the solution which may be a cell culture solution in microwell 101. Whereas microwell 101 will function properly in any orientation, for the purposes of illustration in FIG. 1 pad 103 and pad 104 are shown attached to the bottom of microwell 101.

In an example disclosed herein, the macromolecules to be analyzed are antibodies produced by cells in a host as an immune response of that host to an antigen. This illustrates an embodiment of the invention as detailed under "ALTERNATIVE EMBODIMENT 2" OR "ALTERNATIVE EMBODIMENT 3" in the "EMBODIMENT" section for determining the structure of 2 constituent macromolecules of a cis protein complex where the 2 copies of each constituent, heavy and light chains, are held together by multiple covalent bonds. In this case, there is a polymorphic difference in the heavy and light chains of each antibody in each B cell generated during the immune response. By practicing the present invention, the combination of the antibody's heavy and light chain primary structure can be determined for each cell analyzed e.g. B cell or plasma cell analyzed. Since such a combination ensures exquisite specificity of the antibody, knowing the primary structure allows one to immortalize the antibody by synthesizing an appropriate construct based on the knowledge of primary structure of the heavy and light chain combination of an antibody and by importing such a construct into an appropriate expression system for unlimited supply of the antibody, which finds diverse applications in a variety of fields including research, diagnostics and therapeutics.

In another embodiment detailed under "PREFERRED EMBODIMENT" or "ALTERNATIVE EMBODIMENT 1", not only the primary structure of the heavy and light chain for each antibody is determined, the antibodies produced by each antibody producing cell such as a B cell are captured to form an addressable array in registration with the microwells where the original B cells are each confined. A preparation of fluorescently labeled antigen can be used at varying concentrations to interrogate antibodies captured at each spot such that both the dissociation constant ($k_{off}$) and equilibrium constant ($K_D$) are measured. The association constant can be derived from both $k_{off}$ and $K_D$. Such kinetic binding properties are extremely valuable in ranking the antibodies obtained using the present invention since a large number of antibodies should be recovered in and a means of classifying them is desirable. Furthermore, in the event of an inadequate enrichment for antigen-specific B cells using flow cytometry, these measurements will serve to filter out data deriving from contaminating non B cells or non antigen-specific B cells.

Though the discussion focuses on mouse antibodies, it is clear that the present invention can be applied to antibodies produced by animals with the ability to generate a humoral immune response. In an aspect of the invention a prerequisite for practicing the present invention is the knowledge of the sequence of the constant region for the heavy and light chain mRNA of an antibody for a given isotype. Since the present invention obtains mRNA and proteins directly from antibody producing cells such as B cells, it clearly obviates the need for cell fusion to generate hybridoma cells.

Though the aim to obtain antibodies with the highest $K_D$ and the lowest $k_{off}$ is in line with pharmaceutical development, the present invention can be used to follow an immune response by taking antibody producing cells such as plasma cells and/or antigen specific B cells from any day after immunization. Furthermore, the present invention can be used to monitor the state of the immune system by profiling the B cell population without selection from mouse spleen or even those B cells in circulation for a human subject. This could be very useful in studying autoimmune diseases and to discover biomarkers or potential drug targets. Certainly, the T cell receptors having a structure similar to antibodies can be analyzed in a similar fashion for studying immune functions.

Although only the mouse IgG1, IgG2a, and IgG2b isotype heavy chain conserved sequence and the κ light chain sequence are used for capturing the mouse antibody mRNA in the example illustrated, this represents an embodiment rather than a limitation of the invention. It is entirely within the scope of the present invention to use spotted microarrays wherein a mixture of oligonucleotide probes comprising appropriate sequences can be attached and used to capture all isotypes.

When examining sequences in the example described herein for obtaining antibodies against an antigen, the frequency of occurrence for a given antibody sequence can be used to estimate the $K_D$ of that antibody due to the phenomenon of clonal selection during an immune response. This estimated $K_D$ can be correlated with the measured value obtained from captured antibodies. This line of analysis can aid in understanding the process of affinity maturation in vivo and ultimately guide a focused and more efficient effort to increase the affinity of an antibody in vitro.

Similar to phage display technology, the present invention can be leveraged to screen constructs in many display technologies, such as yeast display, bacterial display, and mammalian display. The candidate display clones can be enriched from the library analogous to the manner for selecting antigen specific B cells by flow cytometry. Once enriched, these display clones can be separated into microwells just like antigen specific B cells and processed in a very similar way. A change in the capture sequence has to be made appropriate for the display technology used. However, in contrast to many of these display technologies, we can process candidates much more rapidly and can characterize their binding properties en masse if the proteins expressed by the display clones are captured as described under either "PREFERRED EMBODIMENT" OR "ALTERNATIVE EMBODIMENT 1".

The present invention can be used to investigate cis protein complexes in other cell types. For example, many cell surface receptors responsible for signal transduction possess the ability to form cis complexes with other receptors via non-covalent bonds. It is conceivable to use the present invention to examine these receptors and identify qualitative changes on a per cell basis. In this case, characteristics, such as morphology, surface marker expression, or intracellular marker expression, can be recorded on a per cell basis to be correlated with the sequence information for the receptors under investigation. A cell-by-cell comparison between normal and cancer cells can be envisioned. If the relevant proteins are captured, similar analysis with a labeled ligand of the receptors can be performed to understand the binding characteristics of these cis complexes on a per cell basis as well as to quantify the receptors and to identify different combinations on a per cell basis. All these pieces of information can be correlated with the observed characteristics of the cell mentioned earlier. A high content analysis of the cell and its signal transduction machinery can be performed.

Rare cell populations, such as stem cells, can also be analyzed using the present invention to relate candidate macromolecules with the observed phenotypes on a per cell basis.

With a large number of sequences available for a combination of heavy and light chains of a given antibody, it becomes possible to use the positions of the mutation and the measured equilibrium constant to infer the critical amino acid residues of the paratope on the antibody.

With the critical amino acid residues identified, it also becomes possible to infer the epitopes and the structure around the putative epitopes on the antigen. The present invention estimates the free binding energy of the antibody and the putative protein folding. With the potential epitope identified for each antibody, this provides another criterion to classify the antibody obtained for a target antigen. The ability to quickly identify sets of antibodies each against different epitopes on an antigen is an advantage of the invention. This reduces the number of confirmatory tests required given the large number of different antibodies recovered. Deciphering the structures local to the identified epitopes on the antigen can lead to a good understanding of the overall structure of the antigen when the density of the epitope identified becomes high enough. This outcome is also unprecedented. These are all due to the fact that a large number of antibodies can be rapidly recovered using the invention.

Embodiments

Preferred Embodiment

Microwells may be produced by attaching 50 micron (±25%) high walls onto a flat support and binding oligonucleotides pads inside the wells. Cells are distributed over these microwells in such a manner that it allows a single cell to settle into a microwell. A cover that is coated with a material suitable for attaching proteins of interest is placed over said microwells. For example, to immobilize antibodies on the top cover the cover is coated with an antibody specific capture agent such as Protein A or Protein L (Sigma-Aldrich, St. Louis, Mo.).

Alternative Embodiment 1

In alternative embodiment 1 a material suitable for attaching proteins of interest is coated on a commercial microwell array, e.g.: a blank PicoTiterPlate device (454 Life Sciences, Branford, Conn.) containing 50 micron hexagonal wells. Cells are distributed over said hexagonal wells in such a manner that allows a single cell to settle into a well. For example, to immobilize antibodies on the surfaces of the wells one coats the surfaces with an antibody specific compound such as Protein A. A custom oligonucleotide array (NimbleGen Systems, Inc., Madison, Wis.) is placed over said PicoTiterPlate to capture and tag mRNAs.

Alternative Embodiment 2

In alternative embodiment 2 we fabricate microwells by attaching approximately 50 micron walls onto a flat support. Cells are distributed over said microwells in such a manner that allows a single cell to settle into a microwell. A custom oligonucleotide array (NimbleGen Systems, Inc., Madison, Wis.) is placed over said fabricated microwells in order to capture and tag mRNAs. No proteins are captured.

Alternative Embodiment 3

In alternative embodiment 3 a commercial microwell array, e.g.: a blank PicoTiterPlate device (454 Life Sciences, Branford, Conn.) containing 50 micron hexagonal wells, is used to contain the distributed cells. A custom oligonucleotide array (NimbleGen Systems, Inc., Madison, Wis.) is placed over said commercial microwell array to capture and tag mRNAs. No proteins are captured.

Alternative Embodiment 4

In this embodiment two planar surfaces are separated a small distance (e.g.: 50 microns) by a porous structure. One or both planar surfaces are microarrays. The porous structure contains holes large enough to contain a biological cell (e.g.: 50 microns). The porous structure is temporarily affixed to one planar surface, thereby constructing an array of open microwells. Biological cells are dispersed over the top of said microwells in one of two methods: a) stochastic separation, wherein a concentration of said cells is chosen so that only a single cell usually occupies a single microwell when the cells are randomly dispersed above said microwells; and b) deterministic separation, wherein individual cells are caused to move to predetermined microwells. After a period of time (e.g.: 3 minutes) cells above microwells are allowed to enter said microwells due to their increased density. Reagents common to all microwells are introduced to the region above said microwells and reactions occur within each microwell. Small molecules are allowed to diffuse out of said microwells in a short amount of time (e.g.: 10 seconds). Then the second planar surface is placed over said microwells sealing them and allowing reactions to occur over a longer period of time. Said reactions result in a modification of the microarray(s) by chemicals confined to said microwells. After said microarray(s) are deemed modified, the planar arrays are separated and the porous structure removed. Codes fabricated into said modified microarray(s) are used during analysis to associate microwells with measured results. Said codes may be the physical position on a microarray, or a tag caused to be embedded in the analyzed data. For example, in the case of an oligonucleotide array, said embedded tag may be a unique DNA sequence.

Device Embodiment

The invention includes a device, system and/or kit which can be used in carrying out the methodology of the invention. A specific multi-well system can be designed which is comprised of a tray comprising a plurality of wells. Each of the wells is comprised of a side wall, a bottom and an open top. The tray may include any number of wells and preferably includes 96 or more wells, 100, 1,000, 10,000, 100,000, 1,000,000 wells or more. The wells are designed so that they are capable of holding a single cell and the tray surface is designed such that when the cells are placed on and moved about the surface of the tray a single cell is moved into each of the wells.

The system includes a tray top which is comprised of a plurality of areas wherein each of the area corresponds uniquely with each well on the tray. The areas may be planar or protrude outward to provide more surface area. The areas (and optional protuberances) on the tray top are coated with an antibody binding agent such as protein A, protein G, protein L, protein A/G and/or goat anti-mouse IgG antibodies. The coating can include any agent which efficiently and selectively binds to antibodies which are in the well.

Each of the wells may also have coated thereon a polynucleotide, e.g. an oligonucleotide. The polynucleotide may act as a primer to replicate nucleotides in the well after the cells are lysed, for example, in a sequencing reaction.

The device may be in a kit that includes instructions to use the device in accordance with any method described here. Further, the device may be sold with reagents including PCR reagents.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Figure 2:
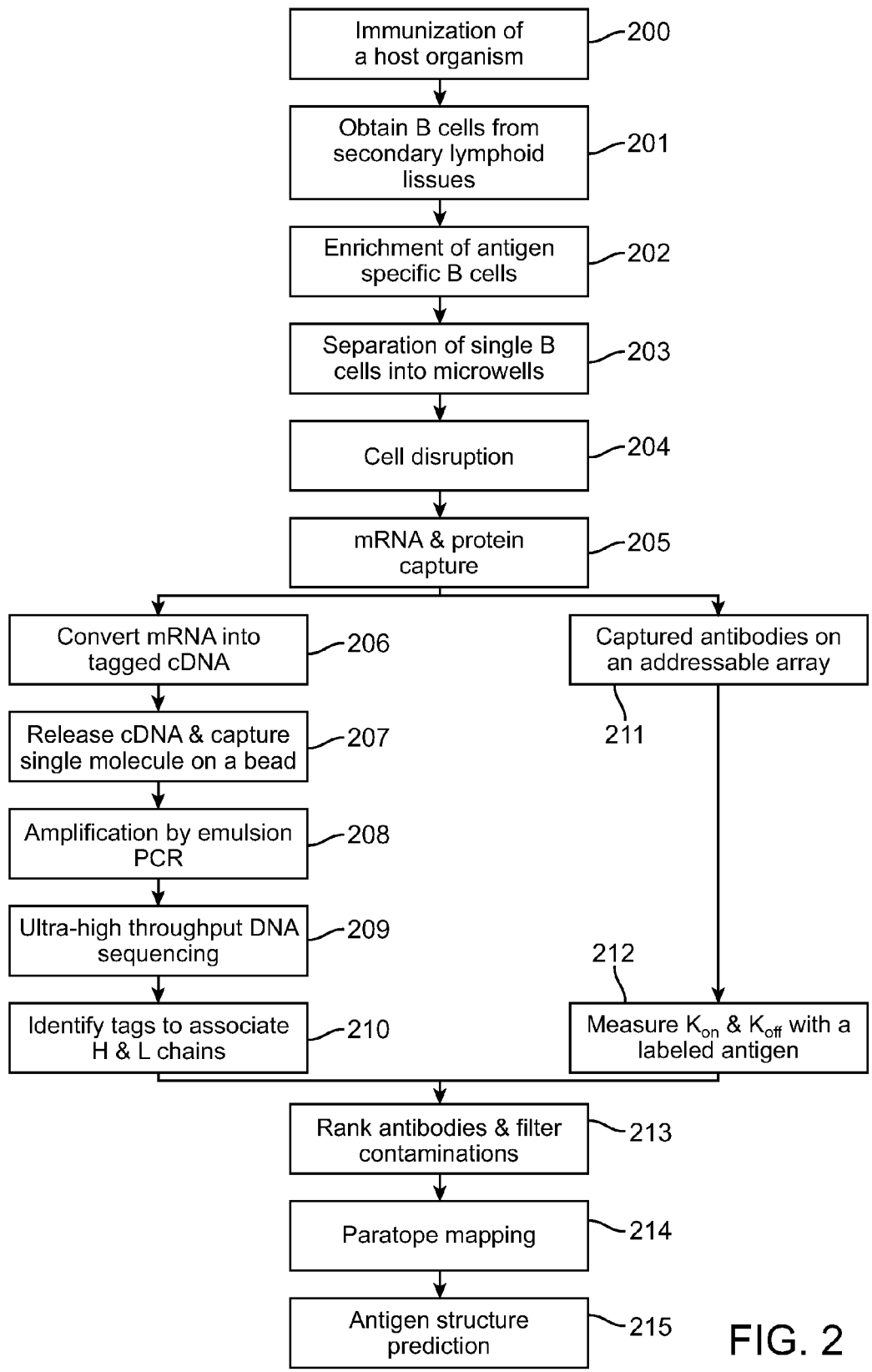
FIG. 2 is a flowchart of a methodology which could be used in connection with the multi-well system of the present invention.

Acquisition of Both the Heavy and Light Chain Sequence for Mouse Anti-HEL Antibodies Immunization of Mice Referring to FIG. 2, a group of BALB/c mice 201 are immunized intraperitoneally with 50 µg of hen egg lysozyme (HEL, Sigma, St. Louis, Mo.) in complete Freund's adjuvant (Sigma). Six weeks after the first immunization, the mice are immunized intravenously with the same dose of HEL. Two days after the second inoculation, blood is taken from the tail vein of the mice and the presence of polyclonal antibodies against HEL in the sera is determined by an ELISA test. If the titer determined by said ELISA test is satisfactory, the mice are sacrificed the next day and their spleens harvested.

Isolation of Antigen Specific B Cells

Cell suspensions of splenocytes are obtained by mechanical disruption of the spleens, and erythrocytes are lysed in 0.16 M chloride ammonium solution at pH 7.4. The resulting single-cell suspensions are stained with a combination of HEL labeled with FITC (Pierce Biotechnology, Inc., Rockford, Ill.) and HEL labeled with PE-Cy5 (Prozyme, San Leandro, Calif.) at optimal dilution. Staining is conducted at 4° C. in 2 steps. First, cells are stained with the FITC-labeled HEL for one hour, using the empirically determined optimal sub-saturating concentration. Cells are then washed three times with FACS buffer. Next, cells are stained with the PE-Cy5 labeled HEL. After staining, cells are washed twice in PBS with 5% FCS.

Cells are analyzed using a modified dual laser FAC-Star$^{PLUS}$™ (Becton Dickinson). Files are acquired using CELLQuest software. In step 202, single B cells with appropriate surface phenotype are sorted for repertoire analysis using the automatic cell-dispensing unit attached to the FAC-Star$^{PLUS}$™ and Clone-Cyt software (Becton Dickinson). Cells are sorted into an appropriate volume of PBS supplemented with an RNase inhibitor, SUPERase-In, at a concentration of 1 U/μL. Alternatively, antigen-specific B cells can be isolated using magnetic-assisted cell sorting (MACS) using reagents identifying appropriate cell surface markers. In addition, antigen-specific B cells can be isolated by agarose gel microdrops using a CellSys 101 microdrop maker (One Cell Systems, Inc., Cambridge, Mass., USA) or microdroplets resulting from water-in-oil emulsion. Alternatively, a combination of the methods mentioned thereof can be used to isolate antigen-specific B cells.

Cell Separation Using PicoTiterPlate (Steps 203)

A PicoTiterPlate (PTP) device (454 Life Sciences, Branford, Conn.) is prepared and the surface coated with Protein L (Pierce Biotechnology, Inc., Rockford, Ill.) in 0.1 M sodium acetate overnight. The surface is blocked with 3% BSA in PBS for 1 hour. After removing 3% BSA in PBS, the surface is washed 4 times with 0.1% Tween-20 in PBS. The PTP device is then filled with PBS supplemented with SUPERase-In. Air bubbles that might remain in the wells are dislodged by centrifugation, once the PTP device is in the Bead Deposition Device (454 Life Sciences, Branford, Conn.). Using a 2-mL pipette, cells are gently placed on top of the PTP device and let sit for 10 minutes to allow individual cell to fall into a well. Cells that do not go into a well are moved off the PTP device with a coverslip. Cells are lysed with a customary lysing solution including a chaotropic agent such as guanidinium thiocyanate or a detergent such as NP-40 (step 204). If capturing of the protein of interest is desired, the detergent NP-40 is to be used. A solid surface coated with a capture agent such as protein A or protein L is used to cover the microwells to confine diffusion of macromolecules released from the lysed single cell and to simultaneously capture said proteins of interest such as antibodies on the solid surface forming a protein array (step 211).

Fabrication of Patterned Photoresistant Structures and Membranes.

Arrays of cylindrical posts of photoresist are fabricated on silicon wafers using standard photolithographic techniques and rigid chrome masks. The arrays of square features measuring 50 μm×50 μm×50 μm with the inter-feature spacing of 50 μm are fabricated using transparencies as photomasks.

Fabrication of Elastomeric PDMS Membranes.

The PDMS prepolymer (mix in a 10:1 ratio with a crosslinking catalyst) is spin-coated on the bas-relief of patterned photoresist features mentioned above at 3,000 rpm for 60 second to generate a film that is ca. 45 μm thick. As such, the resulting PDMS membrane possesses square holes defined by the dimension of the photoresist features. The PDMS membranes are cured for 2 h at 60° C. A thicker layer of PDMS prepolymer is added to the edges of the membranes in dropwise fashion. The membranes are kept at 60° C. overnight. The membranes are removed from their supports using tweezers and are cut to the desired sizes along the edges of the support.

Coating the Holed Membranes with BSA to Minimize Non-Specific Binding by Proteins The PDMS membranes are placed on the surface of a glass slide with a few drops of ethanol. Drops of a buffered solution of BSA (1% w/v, in PBS) are placed on the membrane to cover the holes. Since the fluid does not readily fill the hydrophobic pores, a vacuum (ca. 500 mTorr) is applied for 30 seconds and released twice to extract the air trapped in the holes and the BSA is allowed to adsorb to the surfaces for 15 min. The PDMS membranes on the glass slides are then rinsed three times with PBS. The membranes are peeled from the glass slide in the presence of PBS and transferred to a protein array slide (Full Moon BioSystems, Sunnyvale, Calif.) covered with PBS to help seal the membrane onto the slide.

A Glass Slide Coated with Protein L to Support a Holed PDMS Membrane.

SuperEpoxy 2 glass slides (TeleChem International, Inc., Sunnyvale, Calif.) are coated with Protein L (Pierce Biotechnology, Inc., Rockford, Ill.). A prepared holed PDMS membrane is positioned on top of the glass slide and is pressed to make uniform contact with the surface. The entire setup is blocked again in a buffered solution of BSA. Again, brief vacuum is applied to remove air trapped in the holes. Blocking is performed for 1 hour, followed by washing three times with PBS. The glass slide coated with protein L supporting a holed PDMS membrane is now ready to capture antibodies from B cells and holes on the PDMS membrane are representative of microwells. In addition to Protein L, it is possible to use Protein G, Protein A/G, goat anti-mouse IgG antibodies, etc.

General Features of the Probes on NimbleGen HD-2 Microarray Chips

Figure 4:
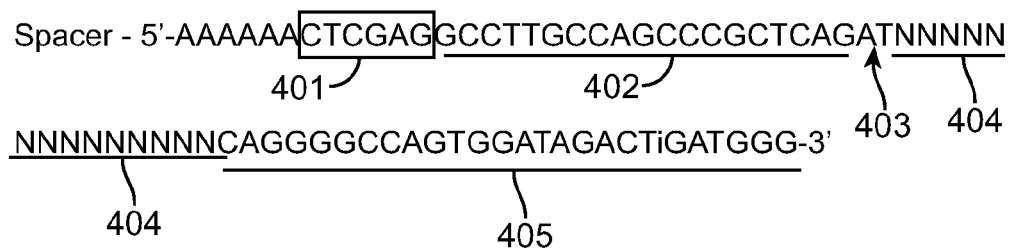
FIG. 4 depicts the features of 2 oligonucleotide probes for capturing mRNA from antibody-producing cells, one for the mouse heavy chain (top) (SEQ ID NO:1) and one for mouse light chain (bottom) (SEQ ID NO:2). 401 and 406 are a recognition site used for cleaving the synthesized cDNA off the microarray by the endonuclease XhoI. 402 and 406 are the primer sequence to be used for PCR amplification. 403 and 408 are landmark dinucleotides to enhance distinction between the PCR primer and the unique 14-nucleotide tag containing the error-correcting Hamming codes denoted by Ns (404 and 409). 405 is the oligo complementary to the mouse heavy chain mRNA constant region including isotypes 1, 2a, and 2b. In addition, 410 is the oligo complementary to the mouse kappa light chain mRNA. There is a spacer and 6 deoxyadenosine residues to get the capture oligo away from the surface of the microarray for better capture efficiency.
Figure 4:
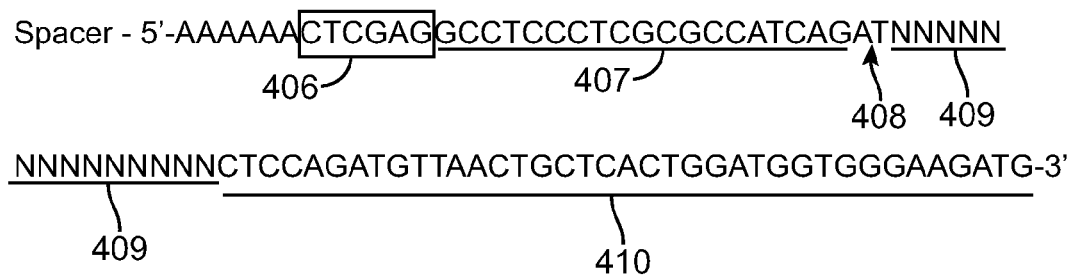

The NimbleGen HD-2 microarray chips have 2.1 million probes on a single slide with the array size of 62 mm×14 mm. As such, there is a potential to have 2.1 million unique tags. To facilitate capture, tagging, and subsequent DNA manipulation, general features of a probe for both heavy chain and light chain are utilized wherein an example of said general features for a heavy chain capture probe are: XhoI cleavage, Primer B by 454 Life Sciences, a 2-base Spacer (always constant) to identify the start of the well identifier tag, a 14 mer well identifier, a mouse gamma heavy chain CH1 IgG1, IgG2a, and an IgG2b isotype heavy chain conserved sequence capture probe. Furthermore, an example of said general features for a light chain capture probe are an XhoI cleavage site, Primer A by 454 Life Sciences 407, a 2-base spacer (always constant) to identify the start of the well identifier tag, a 14 mer well identifier tag, and a mouse kappa light chain constant region capture probe. Note that the length of the microwell identifier tag is a 14-mer, which has a possible sequence combination of over 268 million, far in excess of what is need for 2.1 million probes. This cushion allows elimination of undesirable sequences such as consecutive triples of the same base and perfect self-complementarity or complementarity between the microwell identifier and heavy chain probe sequence, light chain probe sequence, 454 primer A, or 454 primer. In addition, it is desirable to keep the G+C content between 40-60%. If necessary, a parity code, such as one used in Hamming codes, can be embedded in the well identifier for error-correction purposes. Examples of probes for immunoglobulin heavy chain (SEQ ID NO:1) and light chain (SEQ ID NO:2) polypeptides may be found in FIG. 4.

Figure 3:
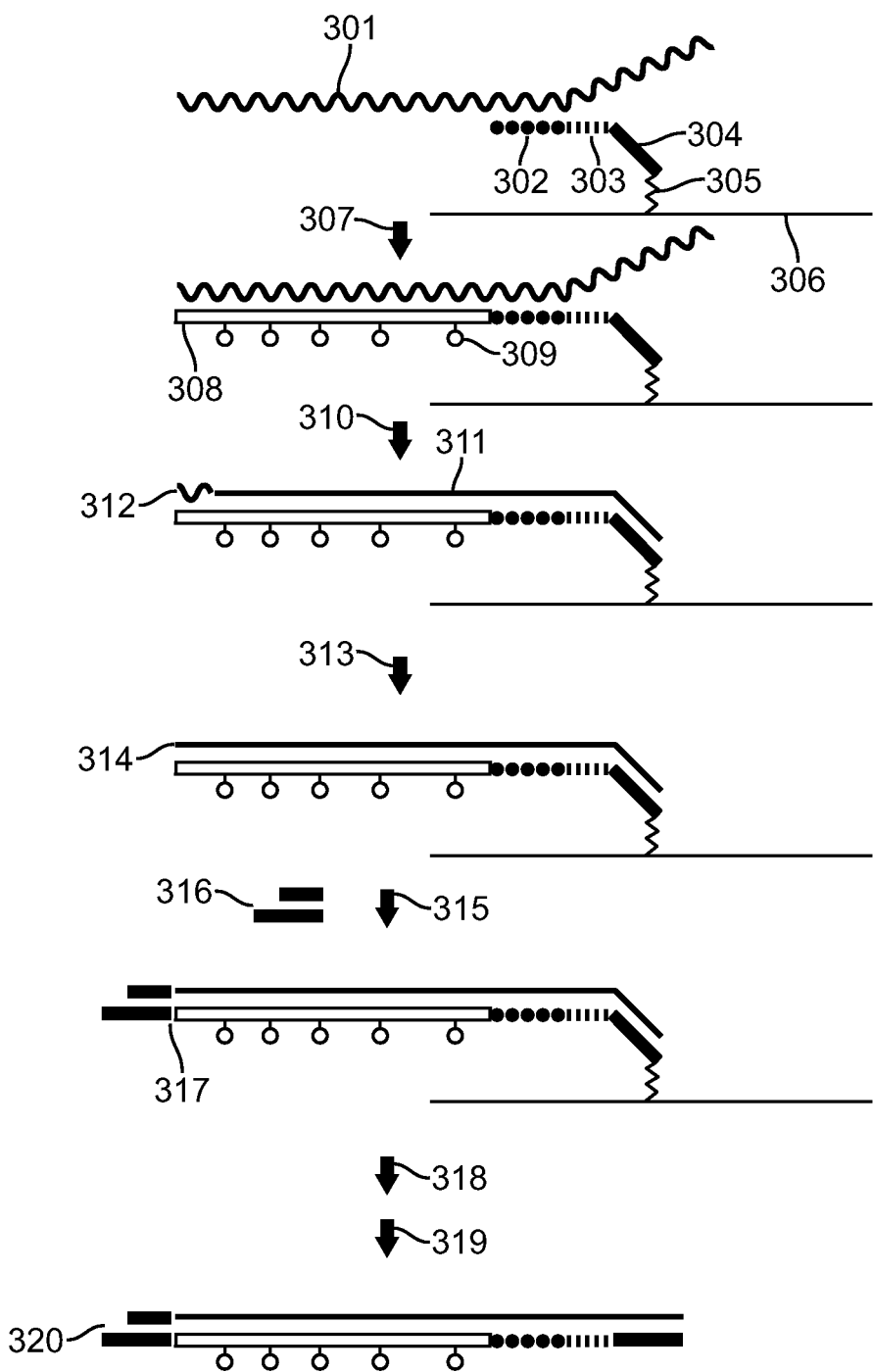
FIG. 3 is a schematic representation of mRNA capture and subsequent conversion into tagged cDNA.

The process of capturing released mRNA from lysed cells and conversion into a tagged ds cDNA is illustrated in FIG. 3. A target molecule of mRNA 301 hybridizes to an oligonucleotide probe 203, which is attached to solid surface 306 as in a typical microarray slide comprising non-DNA linker 305, PCR/sequencing primer B of 454 Life Sciences 304, a well identifier tag 303, a capture oligonucleotide 302 complementary to a region in the target mRNA from either the heavy or light chain gene. Reverse transcription 307 uses a reverse transcriptase (Stratagene, La Jolla, Calif.) to synthesize the first strand cDNA 308 by extending the capture oligonucleotide 203 as a primer and copying an appropriate region of the target mRNA template thereby incorporating 5'-methyl dCTP 309. Second strand cDNA reaction 310 replaces the target mRNA by a combined action of RNaseH and *E. coli* DNA polymerase I, leaving behind a small segment of the original mRNA template at the 5' end. Reaction 313 using T4 DNA polymerase blunts the 5' end of the ds cDNA 314. In a ligation reaction 315, an adaptor molecule 316 comprising PCR/sequencing primer A of 454 Life Sciences with a 3' protruding end to insure orientation specific ligation is attached. In process 318, excess adaptor molecules are removed and in process 319, the attached ds cDNA is cleaved off the solid surface by endonuclease XhoI (New England Biolabs, Ipswich, Mass.), releasing the ds cDNA molecule 320 with the well identifier tag flanked by 454 Life Sciences's PCR/sequencing primers A and B ready to be plugged into the 454 sequencing workflow.

mRNA and Antibody Capture (Step 205)

An equal volume of 1% NP-40 is pipetted from one side of the PTP device to make the final NP-40 concentration at 0.5%. The PTP device is incubated for 10 seconds. The top of the PTP device is then covered with the NimbleGen HD-2 microarray chip, which is securely clamped down using an appropriate device. Incubate at 37° C. for 30 minutes. The entire setup is then soaked in RNase free PBS held in a tray to separate the microarray from the PTP device. Wash the PTP device extensively with PBS for 3 times. PTP device now having the antibodies captured from single B cells can be stored at 4° C. The microarray was soaked in PBS held in a tray at 60° C. for 10 minutes to remove non-specifically hybridized RNA species, then extensively washed with PBS for 3 times. The microarray is now ready for downstream manipulation.

cDNA Synthesis and Adaptor Attachment (Step 206 in FIG. 2)

The microarray is briefly blotted dry on a piece of kimwipe and 30 µL of reverse transcriptase (RTase) reaction solution containing SuperScriptIII RTase (Invitrogen, Carlsbad, Calif.), appropriate buffer components, and dNTPs except 5'-methy dCTP is immediately added. A cover slip is added and the microarray is placed at 50° C. for 1 hour in a humid environment. The cover slip is removed by soaking in DNA polymerase buffer and wash 3 times. The chip is again blotted dry on a piece of kimwipe. Thirty µL of appropriate buffer containing *E. coli* DNA polymerase and RNaseH is added, and the samples incubated at 16° C. for 2 hours. The chip is washed and the synthesized double-stranded (ds) cDNA is polished by T4 DNA polymerase for 30 minutes at 37° C. Pre-annealed adaptors with a biotinylated end are added and ligated to blunt-ended cDNA on the chip by T4 DNA ligase at room temperature for 1 hour in an appropriate buffer. Excess adaptors are then removed by extensive washing in 10 mM Tris-HCl (pH 7.5), 0.1 mM EDTA. The slide with the cDNA attached can be stored at 4° C.

Marker Cells for Registration Between the DNA Pads on the Microarray Slide and the Protein Spots on the Protein Array The hybridoma line TIB-228 (American Type Culture Collection, Manassas, Va.) produces an antibody against human CD14 with the isotype IgG2b. The DNA sequence has been determined for its heavy and light chains (GenBank accession number for heavy chain variable region and light chain variable region is AY669065 and AY669066, respectively). Recombinant human CD14 can be obtained commercially (Abnova, Taipei, Taiwan). When practicing the present invention, an appropriate number of cells, in the range of 10 to 50, can be mixed with the enriched antigen-specific B prior to separating them into microwells. CD14 can be labeled with PE-Cy5 to be distinguished from anti-HEL antibodies, which will be stained with FITC-labeled HEL.

DNA Sequencing by 454 Life Sciences's Technology

The double stranded (ds) cDNA attached to the NimbleGen chip is cleaved off (step 207) by incubating at 37° C. for 15 minutes with XhoI endonucleases (New England Biolabs, Ipswich, Mass.). The released ds cDNA can be optionally captured by streptavidin beads (MyOne beads, Invitrogen, Carlsbad, Calif.) and stored. Such a strategy minimizes DNA loss during storage. Afterwards, the complementary strand can be melted off the beads and quantified using real time PCR by a 454 primer A and light chain primer with an appropriate probe located within the light chain region Similar reagents for real time PCR can be designed for the heavy chain ds cDNA.

Once the ds cDNA is quantified, an appropriate amount is retrieved and mixed with appropriate amount of beads for subsequent emulsion PCR in step 208. The beads are processed and sequenced according to the vendor's recommendation (step 209). Including the spacer, the tag, the constant region, and the entire variable region, both the heavy and light chains require about 415 bases of sequence, which is within the limit of the 454 sequencing technology. Sequencing reads in one orientation are sufficient to obtain unambiguous sequence information to reconstruct the heavy and light chains for an antibody. This is because the genomic sequence of the prototype variable sequence is known. Furthermore, it is likely that FR1 are mostly unmutated in the antibody sequence during immune response based on other reported sequences. Finally, the redundancy of the sequence reads per antibody is high. Thus, based on the vendor's specification of 1 million reads per run, it is possible that one can analyze up to 200,000 B cells minus the few marker cells with 5 fold coverage for each B cell. Alternatively, cDNA originating from specific wells identified by binding kinetics measurement can be directly amplified by incorporating a tag specific sequence at the 3-end of the PCR primer.

After a sequencing run, the following steps are performed to analyze the sequence (steps 210 and 213):
a) A list of sequences from a 454 run is obtained;
b) The sequences are computationally evaluated and the tag, spacer, and constant region for each sequence identified, thereby determining whether each sequence is an H or L chain sequence. In addition, bases toward the 5' end of the heavy chain constant region are sequenced and the minute variation therein used to determined the isotype of the captured antibody;
c) The constant region sequence and spacer are masked;
d) The marker cell H and L chain sequence are identified;
e) The tags corresponding to the marker cell H and L chain sequences are identified and examined to determine if they are in close proximity (i.e.: less than a microwell width) on the microarray. If affirmative, these tags identify a microwell. Locations of multiple microwells containing marker cells will establish the physical layout of the other microwells that each may contain a B cell;
f) Based on the layout, a tag group for each expected microwell is generated;
g) Sequences with identical H chain or L chain are identified;
h) The corresponding tag for the identical H chain or L chain sequences are computationally evaluated. If the tags are identical, then the origin for that H chain or L chain is confirmed;
i) Using the tags from confirmed H chains and confirmed L chains, the pairs of H tag and L tag are reviewed to see if they fit into expected tag groups. If affirmative, the combination is confirmed;
j) Multiple H chain sequences or L chain sequences are aligned in a confirmed combination to obtain a consensus sequence. The consensus will be matched with the prototype genome sequences of the appropriate immunoglobuliln v genes;
k) All CDRs and FRs on the paired H chain and L chain sequences are identified. In addition, identify mutated residues compared with the prototype;
l) Confirmed combinations are clustered and the frequency for identical combinations tallied to determine if they represent the outcome of a clonal selection event; and
m) The DNA sequence is translated into amino acid sequence.

Example 2

Fabrication of Epoxy Wells

The construction of approximately 50 micron chemically inert structures is common knowledge to those skilled in the art. They are used in both Embodiment 1 and Embodiment 3, above, of this invention. Briefly, a 34 mm coverslip (Fisher Scientific, Pittsburgh, Pa.) is washed in acetone, isopropanol, methanol, deionized (18 Mohm) water and dried under a stream of nitrogen. It is further cleaned by exposure to at 120 watt oxygen plasma with a base pressure of 80 mTorr and oxygen pressure of 120 mTorr for 10 minutes (Technics 500 II Asher).

The clean coverslip is carefully centered on the vacuum chuck of a spin coater (Laurell Technologies, North Wales, Pa.) and SU-8 50 (Microchem, Newton, Mass.) negative photoresist is statically dispensed on the center. The coverslip rotates at 500 rpm for 10 seconds and ramps up to 2,000 rpm over the next 30 seconds. The coverslip is soft baked for 20 minutes at 95° C. and cools at room temperature for 10 minutes.

An emulsion mask is designed using Adobe Photoshop and printed on a Linotronic-Hercules 3300 dpi printer (7.4 micron spot size). The mask is placed in contact with the SU-8 film, covered with a quartz slide to weight it down, and exposed in a Kasper 2001 Contact Mask Aligner for 1 minute at 365 nm and at an intensity of approximately 200 mJ/cm$^2$. The exposed photoresist is baked for 2 hours at 95° C. on a level hotplate, soaked in PM Acetate for 30 minutes, and then cured at 200° C. for 1 hour.

The coated coverslip is soaked in sterile, distilled water overnight and sterilized in 70% ethanol in DI under a UV germicidal lamp for 1 hour. The cover slip is rinsed three times using sterile water and stored for at least 4 hours wet and ready for use. The 4 hour storage time ensures no gas bubbles remain in the wells.

The dimension of 50 microns is chosen so the microwells comfortably contain a single 10-15 micron plasmocyte. Since the Reynold's number is 56 times the fluid velocity in meters/sec, there is no turbulent flow inside the wells. Therefore, once the wells are filled with fluid no gas bubbles enter them.

Example 3

Releasing mRNA from a B Cell Using Guanidinium Thiocyanate (GT)

This example refers to Embodiment 3 and Embodiment 4, above. We calculated results from a molecular simulation computing the diffusion of guanidinium thiocyanate (GT) into microwells and back out again. Simulated GT molecules diffused toward and eventually dissolved the cell membrane of a B cells. We computed 20 images of a typical microwell, each computed at a different time. The difference between the first 10 images was 0.1 second; the difference between the last 11 images was 1.0 second.

At time t=0 second, 2,000 GT molecules were quickly introduced into an equal volume immediately directly above each microwell. This represents a very low concentration of GT (26 µM) and is much lower than the GT concentration needed to lyse cells (1M). Since only 2,000 molecules were visualized and used to measure diffusion, we imagined only a small fraction of the 1M GT as labeled with a reporter and only those reporter molecules were used in our calculations. As time progressed over 400 molecules diffused into microwells until t=1.0 second. Then the number of GT molecules above the microwell was quickly reduced and maintained at zero. Said molecules inside the microwells diffused out of the microwells, and after 10 more seconds the concentration fell to 13 molecules.

In our simulation, between 0.5 and 0.8 seconds the cell membrane of plasmocytes substantially dissolved, as did the membrane surrounding the Golgi bodies. Since said mRNA was substantially larger than GT it diffused much more slowly.

The number of GT molecules used in this simulation can scale to any convenient concentration. If we normalize to the concentration loaded above physical microwells, 21% will diffuse into microwells in 1.0 second, and 10 seconds after flushing the concentration above the microwells, the concentration inside the wells will fall to 0.65%. At time equal 11 seconds all mRNA is still completely contained within the wells. GT at this low concentration does not interfere with the hybridization of RNA to DNA, or DNA to DNA. The microwells are sealed after 11 seconds so that all mRNA continues to remain inside the microwells.

The diffusivity was calculated from the Stokes-Einstein relation:

$$D = \frac{k_B T}{6\pi \eta r}$$

where D is the diffusivity, kB is Boltzman's constant (1.38×10−23 J/K), T is room temperature, η is the viscosity of the buffer (8.94×10−4 Pa/sec), and r is the radius of gyration of GT (5.0 Angstrom) or mRNA (60 Angstrom), respectively.

Trajectories were recomputed every Δt=3 milliseconds adding a vector of length $\sqrt{6D\Delta t}$ in a random direction chosen from a 482 tessellation of a sphere.

Example 4

Mapping Antibody Paratopes (Step 214)

When the cis- and/or trans-protein complexes are antibodies, our invention provides information about a much larger number of them than has previously been available. By associating the sequenced tags with the original microwells, we identify a population of mRNAs produced by B cells as well as their respective heavy and light chain sequence. Said sequences can infer the somatic mutations inside each B cells.

We simulated a population of B cells from the published sequences of 21 light and heavy chain antibodies. The sequences were aligned according to recommendations at Web Antibody Modeling. Each sequence was stored with its dissociation constant as measured by Milstein. We also calculated a copy number which represents the number of cells containing a specific mRNA with sequence.

We examined the variation in amino acids along the length of the light chain the heavy chain independently. At every amino acid location, we computed the probability of an amino acid being different from the most frequent amino acid. If at position i we count f most frequent amino acids out of n, then the probability is computed as:

$$p_i = 1 - \frac{f}{n}.$$

The most variable light and heavy chain amino acid are the most likely locations of the paratope. The paratope can be inferred because we can align a population of sequences.

Our invention can also measure the $K_D$ of the antigen bound to the paratope, and we can plot the relationship between $K_D$ and probability of amino acid mutations. In this invention, we interpret clusters in the $K_D$-mutation graphs as evidence of significant immunological activity. When the immune system has found a stable heavy or light chain antibody structure small single-base mutations indicate that it can significantly improve specificity by mutating a single amino acid. Conversely, a single cluster with low $K_D$ indicates discovery of a successful somatic mutation. We strongly associate evidence of successful somatic mutations with paratopes.

Example 5

Antigen Structure Prediction (Step 215)

Although great strides have been made by computational chemists, current methods to computationally infer protein tertiary structure using only knowledge about the amino acid sequence and solvent is still challenging, time consuming and error prone. However, significant improvements in computation time and accuracy are available if prior information or constraints are incorporated during putative folding. The Web Antibody Modeling, University of Bath, UK, has demonstrated antibody models with a high degree of success. Our invention uses the computed structure of the antibodies we discover, and the paratopes identified in example 4 above, to assign realistic probabilities to putative protein folds.

The original Dead-End Elimination (DEE) algorithm identifies several thousand putative protein foldings. Recent improvements have sped up this algorithm and provided structural and statistical filters that significantly reduce this number to approximately 1,000. The run time is approximately 5.5 hours.

The present invention can computationally estimate the free binding energy of the antibody and the putative protein folding. To compute this energy estimate, we computationally dock the antibody with the putative protein. There are many methods of doing this, utilizing shape, electron density, or statistical frequencies. Large computing clusters significantly improve computation time. Typical run times on large computers run approximately 8 seconds per docking.

Our invention compares the computational estimate of free binding energy to the measured $K_D$ and chooses the protein and epitope that most closely matches. The result of our invention is: a) a population of digitally immortalized antibodies against a specific antigen by obtaining the DNA sequences of their H and L chains; b) kinetic metrics of the interaction between each antibody and the antigen; c) computational mapping of the paratopes of each antibodies; d) computational mapping epitopes on the antigen; and e) modeling of the structure of the antigen aided by combining information from a), b), c) and d).

Example 6

Inference of $K_D$ from Sequence Frequencies and FACS Fluorescence

This example refers to Embodiment 3 and Embodiment 4. The surface of each B cell contains thousands of identical membrane bound B-Cell Receptors (BCRs), and to a lesser extent plasmocytes do as well. We can specifically label them by subjecting the cells to a known concentration of fluorescently labeled antigen which will bind to a fraction of the BCRs, said fraction f being closely approximated by the expression:

$$f = \frac{[a]}{K_D + [a]}$$

where $K_D$ is the dissociation constant and [a] is the concentration of antigen.

The fraction f can be estimated by the fluorescence signal. However, large errors are introduced because cells vary in size. Estimates of f can be greatly improved by normalizing said fluorescent measurements by the size the of the cell, a dimension well correlated with forward scattered F1 signals from an appropriate cell sorting instrument, such as one from BD Biosciences, San Jose, Calif. Reversing the above formula, since we know the concentration of antigen [a] used to label the cells, the $K_D$ can be estimated from the normalized fluorescent signals f as:

$$K_D = \frac{[a](1-f)}{f}$$

Our invention distributes cells into microwells and captures DNA complementary to mRNA on uniquely tagged oligonucleotides. It is ordinarily difficult to associate the $K_D$ inferred by FACS fluorescence with a tagged oligonucleotide since the cells are pooled prior to said distribution. One way our invention solves this association is by using the relationship between the $K_D$ and the abundance (or frequency) of B cells expressing a particular antibody: the number of B cells expressing identical antibody molecule n is a function of the KD:

$$n = \frac{c}{K_D^3}$$

where c is an arbitrary constant.

This relationship applies not only to the number of sequences we read from said distributed microwells, it also applies to the antigen positive cells we measure in the FACS. Therefore, the constant c is determined by:
a) determining the number of times each sequence has been sampled;
b) using an arbitrary value of c, computing the copy number associated with each sequence;
c) sorting the sequences in order of said copy number;
d) normalizing the side-scattered FACS signal F2 by the forward scattered FACS F1 signal to compute and estimate of the bound BCR surface density;
e) sorting the FACS signals by said bound BCR density estimate;
f) adjusting the parameter c to insure the total number of sequences equals the total number of FACS signals;
g) aligning said sequences with said bound BCR density estimates;
h) computing the $K_D$ for each said bound BCR density estimate;
i) associating with each sequence the average $K_D$ of said bound BCR density estimate aligned with said sequences.

We simulated data from the forward scattered F1 signal of a FACS sort of plasmocytes. We displayed the fluorescent amplitudes and the number of cells counted with a specific fluorescent amplitude.

Starting with our simulated F1 and F2 signals, we followed the procedure labeled as steps a) through i) above. A comparison of the $K_D$ s inferred by our method and $K_D$s reported in the literature were quite good. The reasonably close match of the measured and predicted $K_D$s demonstrates the value of this approach.

Example 7

Optimizing the Number of Distributed Cells

Our invention distributes a certain number of cells over a surface populated by microwells. After a short time, e.g.: 3 minutes, said cells settle into the microwells. There is a competition between having as many microwells, and therefore as many cells, as possible, and leaving the microwells large enough that a) sufficient mRNA is captured by tagged oligonucleotides, and b) material from the cell's interior does not substantially interfere with mRNA-DNA hybridization. We anticipate that for cells with a diameter of 10-15 microns such as B cells, a 50 micron well size is a reasonable compromise. Clearly for other cells or different chemistries, the well size may vary.

Once the size of the microwells is fixed, the number of microwells must be determined A convenient dimension for the entire array is the size of a microscope cover slip, 34×34 mm, of which only 24×24 mm is used in order to allow room for mechanical support. This leaves room for 230 thousand microwells placed on 50 micron centers.

As we distribute the cells over the microwells we would like one cell to settle into each microwell. However, if we spread too many cells over the microwells there will be a high probability that two or more cells may settle in the same well. If we spread too few cells over the microwells, we will leave many microwells without a single cell. The statistical optimization of this problem is well known to those skilled in the art. Briefly, consider a single cell entering the volume immediately above the microwells. The probability p a microwell contains said single cell is $$p = \frac{1}{230,000}.$$

The probability prob that two microwells contain one cells each is, according to the binomial theorem, prob=2p (1-p), since we wish one of the two cells to be in the well while the other cell is anywhere else. For n cells, prob=np $(1-p)^{n-1}$. The number of single cell microwells (singlets) equals 230K times prob. Using the same formalism, the number of unoccupied microwells equals 230K $(1-p)^n$.

To optimize the number of distributed cells, we computed the probability of multiplets m, m=$1-(1-p)^n-np(1-p)^{n-1}$; i.e.: the probability that a microwell will receive 2 or more cells as a function of number of cells. A customary balance, and the one we use here, between multiplet probability and number of cells is 5% which occurs when n=82,000 cells.

We computed the relationship between number of single cells occupying single microwells and number of cells distributed over the microwells. For example, when the number of distributed cells equals 82,000, the number of single cell wells 57,400.

Example 8

Optimizing the Number of Sequences

Every microwell contains two tagged oligonucleotides to capture Ab mRNAs: one for the heavy chain and one for the light chain. In order to digitally associate these two sequences, at least one molecule from each well containing a cell must be sequenced. Since the cDNA sequences are released and pooled, we must over-sample the sequences to insure at least one sequence from the heavy and light chain of each cell are sequenced.

The population of sequences is twice the number of cells. The probability p of selecting a particular heavy chain sequence equals the probability q of selecting the light chain sequence:

$$p = q = \frac{1}{164,000}.$$

The probability of not selecting a particular sequence is r=1-p-q. The number of wells with both chains sequenced at least once is computed using the multinomial distribution: prob=164,000 $(1-r^n-npr^{n-1}-npq^{n-1})$. The number of wells with both chains sequenced was computed as a function of total number of samples sequenced. A customary over-sequencing rate to insure good coverage is 5×. Using 5×82,000, this number of sequences provides double sequences from 160,000 microwells, for a double sampling percentage of 97.6%.

Example 9

Measuring $k_{off}$ and $k_{on}$ Using Fluorescence Decrease
(Step 212)

The hybridoma line (NQ2-12.4) has a measured $K_D$ of $2.8\times10^{-7}$ molar$^{-1}$. Measured antibody $k_{on}$ values tend to cluster around $10^5$ sec$^{-1}$ molar$^{-1}$, giving a $k_{off}$ of $2.8\times10^{-2}$ sec$^{-1}$. $K_D$s larger than $10^{-7}$ molar$^{-1}$ are of little interest for research, diagnostics or therapeutics because they bind their respective antigen very weakly, dissociate from their antigen quickly, and substantially lower the probability of obtaining desired outcomes. Tight binding antibodies are much more useful, typically with $K_D$s less than $10^{-8}$. Our invention takes advantage of the fact that tight binding $K_D$ s typically have $k_{off}$ values $<2.8\times10^{-2}$ sec$^{-1}$, and therefore easily allow the use of fluorescence to measure $K_D$ and $k_{off}$ in a 24×24 mm antibody array. $k_{on}$ is computed from $$k_{on} = \frac{k_{off}}{K_D}.$$

In this example, we show that our invention works for the extremely weak case of $2.8\times10^{-2}$ sec$^{-1}$ and therefore will work for other commercially interesting antibodies.

In this embodiment, a microscope coverslip is coated with Protein A. Cells are distributed over the microwells, lysed, and said coverslip placed over the microwells. In this embodiment oligonucleotides are affixed to a surface inside the microwells. If a cells lysed in a microwell contains a large number of antibodies, these antibodies will diffuse throughout the well, into the vicinity of the Protein A and tightly bind, as is well known to those skilled in the art. After an incubation time commensurate with the anticipated range of $k_{on}$ and antibody concentration, the coverslip is removed, washed, and subjected to a solution of fluorescently labeled antigen.

We performed a detailed molecular simulation of the binding of NQ2-12.4 to phOX, using the equilibrium expression: Ab·Ant ↔ Ab+Ant. We concentrated on the first 3 minutes after unbound antibody Ab was exposed to two initial concentrations of fluorescently labeled antigen: $[Ant_0]=100$ nM, and $[Ant_0]=200$ nM. The evolution of unbound antibody Ab, bound antibody Ab·Ant and free antigen Ant is summarized by the following well known relationships:

$$\frac{d[Ab\cdot Ant]}{dt} = -k_{off}[Ab\cdot Ant] + k_{on}[Ab][Ant]$$
$$= -\frac{d[Ab]}{dt}$$
$$= -\frac{d[Ant]}{dt}$$

Fluorescently labeled antigens are easily measured and closely approximate the binding of unlabeled antigens. If we start with no bound antigen, after soaking the antibodies in antigen for over 3 minutes the fraction f of antibody sites with bound antigen divided by the total number of antibody sites asymptotically approaches equilibrium as:

$$f = -\frac{[Ab\cdot Ant]}{[Ab\cdot Ant]+[Ab]}$$

$$= \frac{[Ab\cdot Ant]}{[Ab_0]}$$

$$= \frac{[Ant]}{K_D + [Ant]}.$$

If we know the total number of antibodies we could measure the fractional occupancy f directly: we would carefully excite the fluorophores with a well controlled flux of light and count the number of photons scattered into our detector. Based on the fluorescent cross-section and known probability of photobleaching, we could quite closely estimate the number of fluorophores. The difficulty with this approach is we do not know the number of total antibodies, and therefore we cannot form a ratio of measured fluorophores to total fluorophores in order to calculate the ratio f.

Our invention solves this problem by measuring two or more fluorescent amplitudes. The signal from a fluorescent microarray reader is dependent on the concentration of fluorophores. Usually the relationship is approximately linear. If we measure the same total signal from a fixed deposition of antibodies, and properly correct for known photobleaching effects, then the fractional occupancy f is also linearly related to measured fluorescence: $meas_1 = \alpha \cdot f_1$ for some fractional occupancy $f_1$ related to some specific antigen concentration $[Ant_1]$. For the same deposition of antibodies, this is equally true for $meas_2$, $f_2$ and $[Ant_2]$ with the same $\alpha$. Using the relationship for f stated above, we solve for $K_D$ as a function of $meas_1$, $[Ant_1]$, $meas_2$, and $[Ant_2]$:

$$K_D = \frac{meas_2 - meas_1}{\frac{meas_1}{[Ant_1]} - \frac{meas_2}{[Ant_2]}}$$

Although this equation is written as a function of two fluorescent measurements associated with two antigen concentrations, it is to be understood that more fluorescent measurements associated with more antigen concentrations could easily be used by those skilled in the art of non-linear parameter estimation.

Once the $K_D$ is determined we solve for a using $$\alpha = \frac{meas_1}{f_1} = \frac{meas_1(K_D + [Ant_1])}{[Ant_1]}.$$

Knowing $\alpha$ is extremely useful in our invention since we can then convert our measured signals to fractional occupancy. Since we know the number of measured fluorophores from the calibration of the fluorescent reader, the fractional occupancy gives us the total number of antibodies, both bound and unbound. This number correlates highly with the identity of cells, i.e., whether they are plasmocytes or B cells. Plasmocytes often contain additional somatic mutations from their B cell progenitors. Since the B cell receptors on the surface of plasmocytes were created before the somatic mutations, the antibodies may be different. Identifying B cells, as well as identifying high frequency B cells, allows us to better estimate tight binding antibodies.

The above description requires the accurate measurement of both antigen and fluorescent signal. We use the initial concentration of antigen $[Ant_0]$ as an estimate of $[Ant]$. This is generally adequate when $[Ant_0]$ is substantially greater than the concentration of total Ab. As estimates of [Ab], we use an antibody density of 22 fmol cm$^{-2}$ over an area of 50 micron in a volume of 125 picoliters for a concentration of 4.4 nM. Our initial concentrations [Ant$_0$] of 100 and 200 nM are substantially greater than this.

The measurement of fluorescence must be done in a solution with [Ant$_0$]=0 to minimize background noise. We measure fluorescent amplitude as a parameter while measuring $k_{off}$. Fluorescence decreases as antibody bound antigens are subjected to an antigen free solution. In general, it is difficult to measure [Ab·Ant] at time=0 using a coverslip since it takes a finite amount of time to load the coverslip covered by free solution into an appropriate reader while maintaining a flow of antigen free solution over the coverslip. In our invention, we sample the bound antibody concentration by measuring the fluorescence of fluorescently labeled antigen bound to the antibodies at approximately one minute intervals. Modern microarray readers (e.g.: ArrayIt InnoScan 700, TeleChem International, Inc., Sunnyvale, Calif.) scan 25×24 mm areas in one minute at 10 micron resolution, quite sufficient for 50 micron antibody deposits.

For example, phOX antigen bound to NQ2-12.4 decreases quite quickly and represents one of the worst antibodies our invention anticipates measuring since its fluorescent decay time is the fastest we anticipate sampling. Tighter antibodies will have decay times orders of magnitude greater. The microarray reader will image approximately 230,000 antibody spots in approximately one minute and therefore infeasible to image all spots continuously or immediately. Our invention samples the signal decrease three times. Typical fluorescent measurements in digital numbers are: 736 in 0.39 seconds, 137 in 1.39 seconds, and 26 in 2.39 seconds.

In our simulation, we fit the measured data meas to the well known formula for exponential decay: meas=Ae$^{-k_{off}t}$. Using the above data and the non-linear parameter estimation features of Mathematica (Wolfram Research Inc., Champaign, Ill.) we compute A to be 1427 and $k_{off}$ to be 0.028 sec$^{-1}$.

Example 10

Alignment of NimbleGen Oligonucleotide Pads and 454 Hexagonal Wells

This example applies to Embodiment 2 and Embodiment 4, above. NimbleGen oligonucleotide arrays contain staggered oligonucleotide pads 13 microns×13 microns in size. By staggered, it is meant alternating, for example, a chess board, wherein the black squares are staggered. When mating a NimbleGen array with PicoTiterPlate (PTP) hexagonal wells, there will be some oligonucleotide pads that are completely exposed to the microwell, and others that are buried under microwell walls or exposed to multiple microwells. To make our invention work with a NimbleGen oligonucleotide array and PTP hexagonal wells, we must insure that a majority of wells contain at least two pads with a large portion of their area exposed.

We conducted a simulation wherein 100×100 hexagonal wells were constructed on 50 micron centers with a diameter, that is, a distance between opposing walls, of 44 microns. A grid of points on one micron centers was placed over each hexagonal well and only points falling inside each hexagon were selected. For each selected hexagonal well, the number of points in the unique pad containing it (computed by dividing its location by the size of each pad) was incremented. After processing each point we had a data base that listed for each well the pads it contained and the number of points in each pad. Since we knew the maximum number of points in a pad, we computed the fraction of each pad inside each well.

Each well contained at least six pads. For each well we selected the six pads with the largest fractions, creating a 10,000×6 array. Considering this to be 10,000 samples of six numbers, the mean of the 6 fractions and their standard deviations, are: the first mean is 1 with a standard deviation of 0; the second mean in 0.99 with a standard deviation of 0.02; the third mean is 0.93 with a standard deviation of 0.07; the fourth mean is 0.81 with a standard deviation of 0.11; the fifth mean is 0.51 with a standard deviation of 0.15; and the sixth mean is 0.4 with a standard deviation of 0.15.

Every well contained at least one complete pad. 99% contained at least 2 staggered pads. Therefore, our embodiment using NimbleGen oligonucleotide arrays and PTP hexagonal wells allows the heavy and light chains from 99% of the distributed cells to be digitally matched using DNA tags.

Example 11

A Glass Slide Coated with Low Melting Point Agarose

This method is useful when using a robotic microarray spotter (e.g.: SpotBot 2, TeleChem, International, Sunnyvale, Calif.). A 1% low melting point agarose (Invitrogen Corp., Carlsbad, Calif.) solution is dissolved in purified water and poured over the surface of a glass slides at 70° C. (2.0 ml per slide). After gelling of the agarose, slides are dried in air. The dried slide is placed into the microarray spotting equipment and warm water (e.g.: 70° C.) is dispensed onto the agarose. The agarose melts and is washed away with another application of warm water. A hole pattern is fabricated wherein said holes are as reproducible as the microarray spotter's tolerance (approximately 10% for SpotBot 2). Once said holes are formed and cleaned, other molecules can be spotted into the holes using the same microarray spotter. If there is an alignment error, the agarose offer a low resistance to the microarray needle. The final result is a hole whose size is controlled by the warm water injection process, and a uniform coating of detection molecules attached to the glass. The molecules coated onto the glass can be, for example, oligonucleotides, proteins, antibodies, or capture molecules, or a mixture of 2 or more oligonucleotides, proteins, antibodies, or capture molecules.

The generation of unique oligonucleotide tags and their incorporation into oligonucleotides including a region complementary to mRNA and a PCR primer.

One method of fabricating an oligonucleotide array complementary to mRNA utilizes synthesized oligonucleotides. This is difficult when considering arrays with, say, 40,000 or more oligonucleotides each with a unique tag. An efficient method of producing 40,000 oligonucleotides with unique tags comprises:

a) Synthesizing 200 unique oligonucleotides without terminating phosphate groups;
b) Synthesizing another 200 unique oligonucleotides with terminating phosphate groups;
c) Ligating oligonucleotides from step (a) with oligonucleotides from step (b). Note that oligonucleotides from step (a) cannot ligate with one another because of the missing phosphates. Similarly, oligonucleotides from step (b) cannot ligate with one another because of the extra phosphates.
d) Ligating the oligonucleotides from step (c) with the PCR primer.
e) Ligating the oligonucleotides from step (d) with the region complementary to the mRNA.

The value of 40,000 pads is only exemplary and not intended as an additional limitation on the size of the microarray. This example, used in conjunction with a glass slide coated with low melting point agarose, provides a low cost example of Embodiment 5.

Example 12

Alignment Between DNA Chip and Prefabricated Wells

Figure 5:
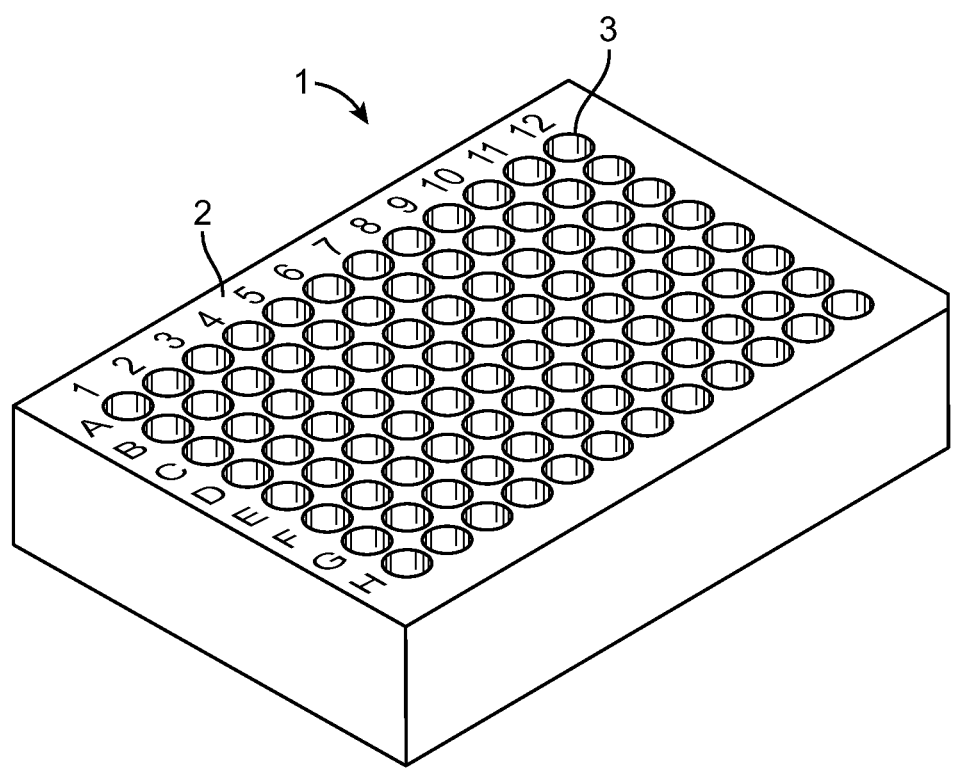
FIG. 5 is a schematic view of an embodiment of a multi-well tray component (1) which could be used in connection with the system of the invention. The wells include indices or addresses 1-12 (2) along the row and indices or addresses A-H (3) along the columns providing a conventional 96 well tray.
Figure 6:
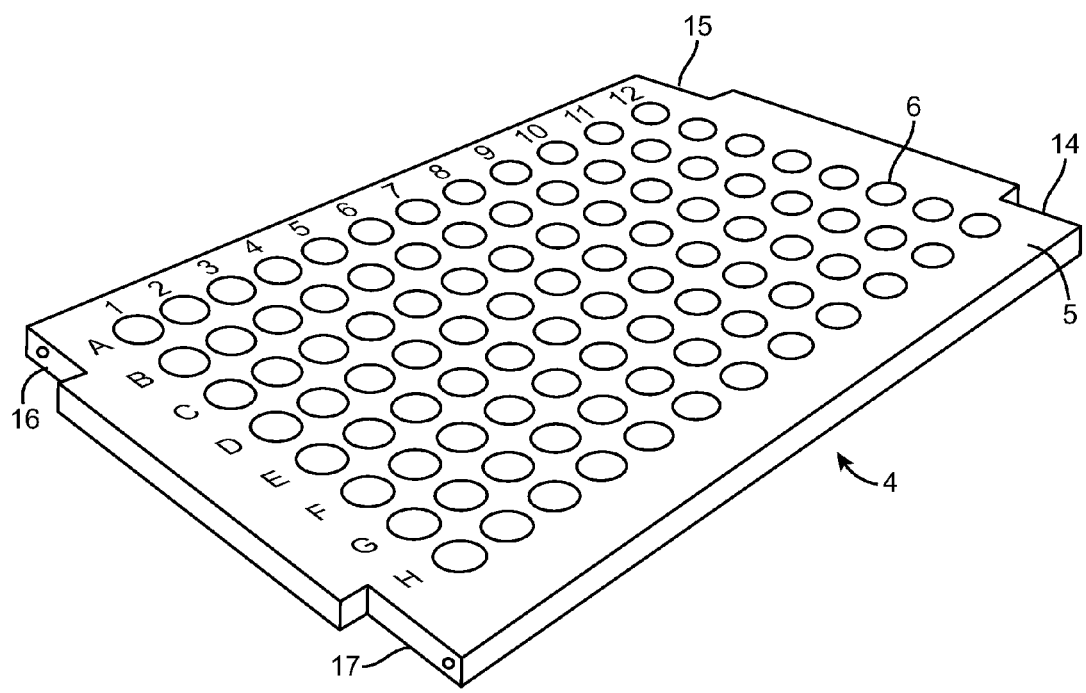
FIG. 6 is a schematic view of a multi-well tray top component which could be used in connection with the present invention. The top 4 is comprised of a basic frame 5 and includes a plurality of areas 6 on the top. Each area 6 is addressed with indices as in the multi-well tray 1 of FIG. 5. The areas are numbered 1-12 along the rows and A-H along the columns as with the tray of FIG. 5. Portions 14-17 are cut out to provide precise alignment with a top component in, for example, FIG. 7.
Figure 7:
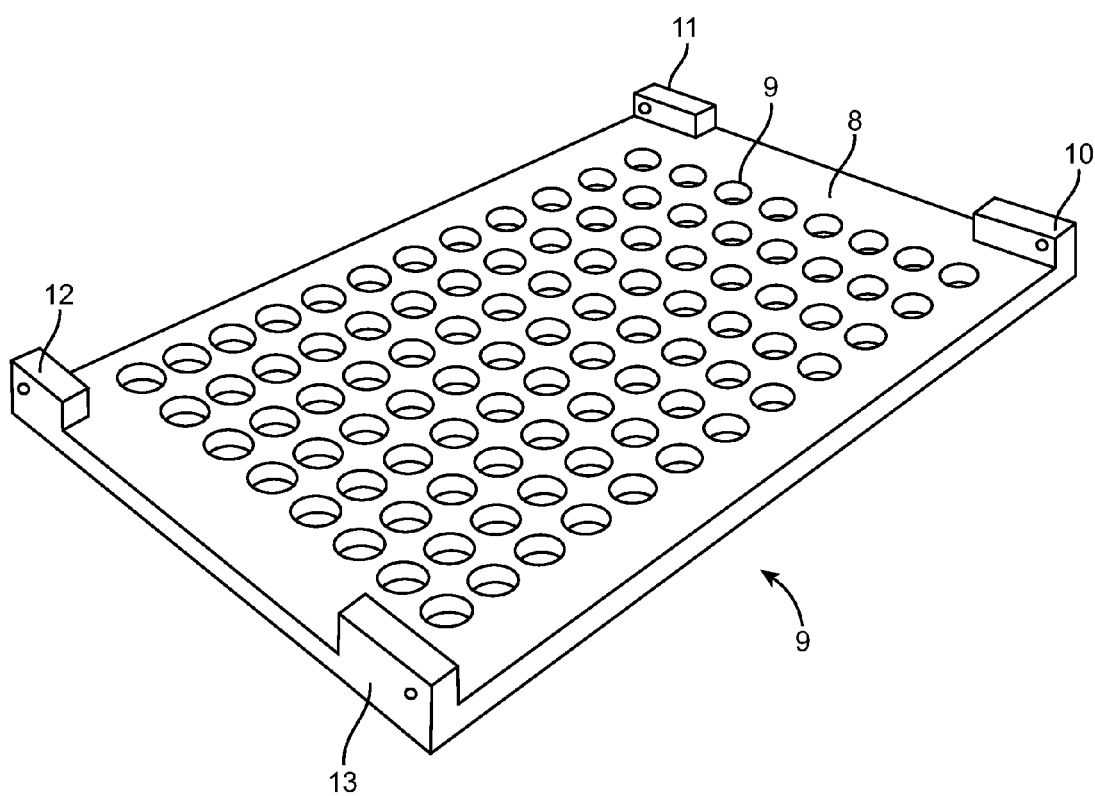
FIG. 7 is a schematic view of a second embodiment of a multi-well tray component which could be used in connection with the top component of FIG. 6. The tray is comprised of a frame 8 which includes a plurality of wells 9. The tray includes upwardly extending notches 10, 11, 12 and 13 in each of the corners. The notches 10-13 fit within the cut-out portions 14, 15, 16 and 17 of the top shown in FIG. 6. In this manner the top and the tray can be precisely aligned with each other.
Figure 8:
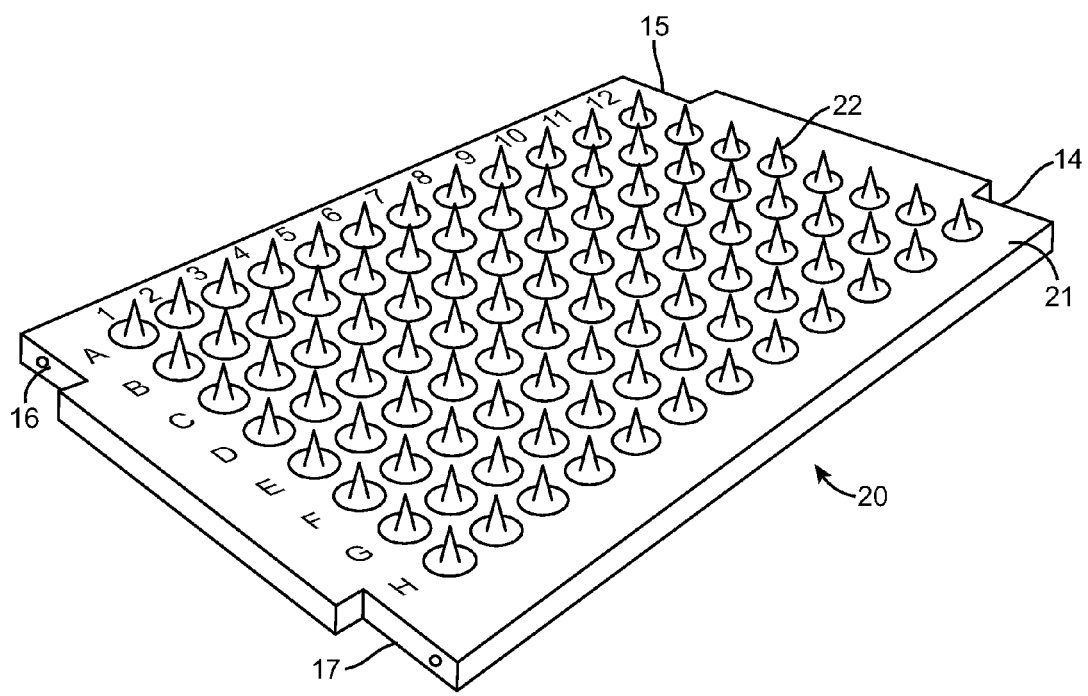
FIG. 8 is a schematic view of a second embodiment of the top which is shown in FIG. 6 wherein the top includes a protuberance on each of the areas. Tray top 20 comprised of a frame 21 and protuberances 22 on each of the areas corresponding to the well 3 of FIG. 5. In the embodiment depicted in this figure, each area includes a single protuberance. However, the area may include 2, 3, 4 or any greater number of protuberances.

SU-8 photoresist (MicroChem Corporation, Newton, Mass., United States) was spin-coated onto a 10 cm silicon wafer in accordance with manufacturer's recommendations. A pattern of 50 micron cubic micro-wells was exposed using ultraviolet light from a mask aligner (SUSS MicroTec AG, Garching, Germany) in accordance with manufacturer's recommendations and developed using SU-8 developer (Micro-Chem Corporation, Newton, Mass., United States). Polydimethylsiloxane (PDMS) (SylGard Elastomer, Ellsworth Adhesives, Germantown, Wis., Unites States) was mixed, cured and removed in accordance with manufactuer's recommendations. The bottom tray (FIG. 5) was formed by using a razor blade to cut out an array of 205 by 154 micro-wells (31,570 micro-wells) and carefully placing it onto a clean and dry microscope slide where it formed a hydrophobic bond with the glass slide. The dimensions and location of the micro-wells exactly matched the location and size of pads of oligonucleotides on a DNA chip (385K CGH array, Roche/Nimblegen, Madison, Wis., United States). The DNA chip formed the top of the micro-wells (FIG. 6) and was placed above the micro-wells so that most wells were directly beneath DNA and most well walls were in contact with bare glass. When micro-wells this small are used, the positioning, alignment, and subsequent sealing of a DNA slide above PDMS wells is sufficiently delicate that mechanical assistance is generally needed, such as a mask aligner or a custom built apparatus.

One example of an available mask aligner is the MJB4 four inch manual mask aligner from SUSS MicroTec AG (Garching, Germany). A glass slide is affixed with mylar tape to a 4" square quartz plate and inserted into the aligner's mask vacuum chuck. PDMS is affixed to a similar plate and inserted into the wafer chuck. The two surfaces are aligned using optics and positioning controls available on the aligner. Once aligned, the PDMS is removed and processing continues until the DNA slide and wells must be aligned. At this time, the PDMS is reinserted into the aligner, the two surfaces (DNA and PDMS) are placed into contact, and the entire assembly is left alone for several minutes while cDNA is constructed from antibody mRNA.

Although this procedure can be carried out it has several drawbacks: 1) The components to be aligned must be pushed into a UV protected area precluding easy access by people and equipment; 2) there are very few places for excess fluid from the necessarily wet cell suspension deposited on top of the wells; and 3) there are expensive features on the aligner that are not needed.

Figure 9:
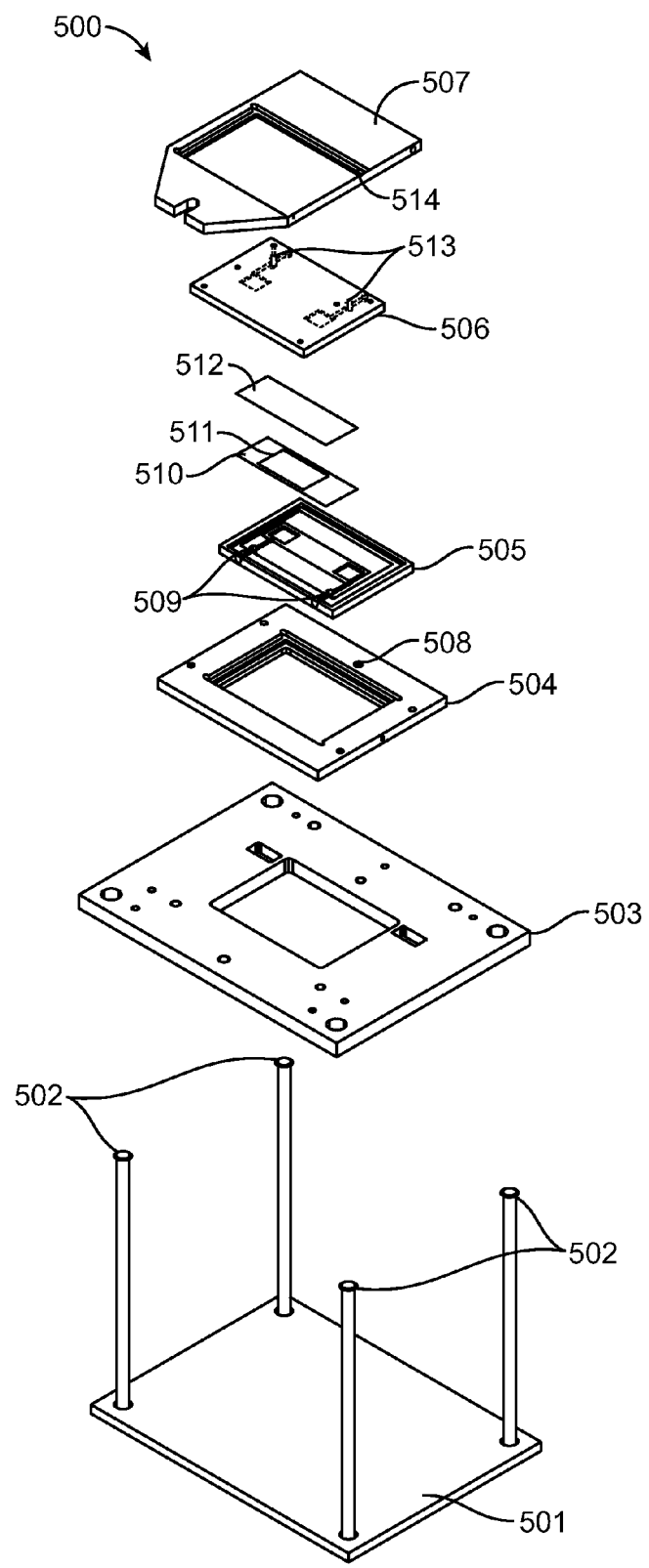
FIG. 9 is an exploded schematic view of a system of the invention showing specific components for aligning the tray with tray tops.

The system can be more efficiently used with a custom aligner designed to contain a small amount of fluid, provide easy access for the experimenter and equipment, while providing a reduced set of functions at a reduced cost. An example of a custom aligner 500 is shown in FIG. 9. Four vertical posts 502 screw into aluminum base plate 501 and support aluminum table 503. On aluminum table 503 sits the bottom pressure plate 504. A first plastic insert 505 and a second plastic insert 506 are sandwiched between bottom pressure plate 504 and top pressure plate 507.

Vacuum port 508 provides close contact between bottom pressure plate 504 and plastic insert 505, as well as top pressure plate 507 and plastic insert 506. The bottom tray, includes micro-wells 511 placed on glass microscope slide 510, and the tray is held firmly to the top side of plastic insert 505 by additional vacuum ports 509. Similarly, a DNA chip 512, having the same dimensions as the microscope slide 510, is held firmly to the bottom side of plastic insert 506 by additional vacuum ports 513.

When bottom vacuum is released, the bottom micro-wells 511 and glass slide 510 can be carefully moved together in two axes by sliding them against plastic insert 509. Once the wells 511 are optimally aligned, vacuum is applied to vacuum ports 509 to keep the slide 510 from moving. A small computer interfaced microscope (not shown) is positioned beneath the aluminum table 503 to image cells in wells using flat field light entering the top of apparatus 500.

Once alignment is achieved, marks are placed on the plastic insert 509 to record the position of slide 510. Alternatively, objects are placed next to the glass slide 510 to record the position of the slide 510. Then microwells 511 and the glass slide 510 can be removed, processed and returned to alignment apparatus 500 within a positional accuracy of 10 microns. It was found that 10 micron accuracy was adequate to correctly align the microwells 511 with the DNA chips 512 so that specific addresses on the chip 512 could be correctly matched to specific addresses of the microwells 511.

Example 13

Embedding Numeric Codes in Microwell Design

During alignment and processing, it is often useful to examine the microwells, or cells in the microwells, under a moderate power microscope (e.g.: 100×). The field of view of the microscope seldom encompasses all microwells. Therefore, it is difficult to know exactly which wells are being viewed by examining a single microscope image either in real time or afterwards from a captured image. It may be desirable to know exactly which wells are being viewed without having to count wells from an edge or corner.

For this purpose, a coded shape such as a particular shape (FIG. 10) may be embedded into the wells. The shape is a tradeoff between three constraints: 1) the shapes should be different enough that epoxy coated wafers can easily reproduce them and, in turn, they can be seen in the PDMS impressions taken from the epoxy coated wafers; 2) the well volume should not be substantially different from well to well so that cells will experience approximately the same microenvironment; and 3) the wall thickness is not reduced in a manner which would weaken the PDMS structure. Fragments of an octagon provided a useful balance between these constraints. Octagon fragments were separated into symmetric or nonsymmetric fragments and used in shapes of FIG. 10.

Figure 10:
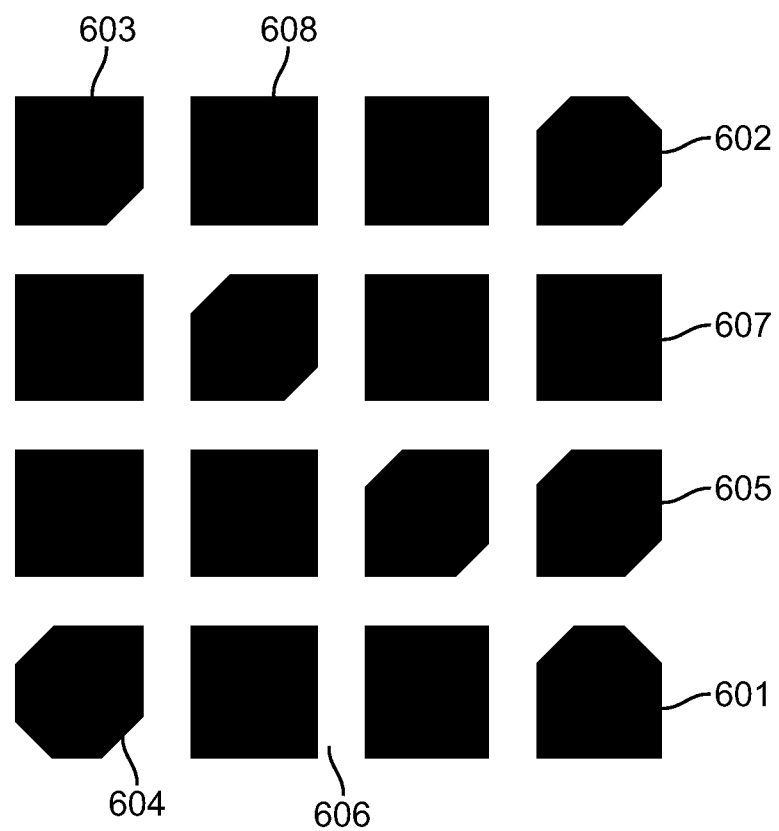
FIG. 10 is a schematic view of micro-wells with different designs and configurations 601-608, which may provide local addressability when the field of view does not encompass all micro-wells.

In this example a 4×4 block of wells was chosen because under our laboratory microscopes we could easily place 16 wells in the field of view. Referring to FIG. 10, a 16 well block 600 is an example of the use of octagon fragments to embed three numbers in the shape of the wells: 1) the row number; 2) the column number; and 3) the pattern number. In this example, there are a maximum of 64 rows and columns, each numbered 0 through 63. Since there are 4 wells in each row and column per block, this example addresses a maximum of 256 wells in all rows or columns of a pattern. Binary representations are used to encode the row and column numbers. As is well known in computer literature, six binary digits are required to encode values 0 through 63. Symmetrical wells are used to represent row and column 1s and 0s. For example, in FIG. 10, well 605 is a 1 and well 607 is a zero.

Nonsymmetrical wells are used at the corners of the block. Well 601 provides a starting point and starting direction. In addition, the other corners (602, 603 and 604) provide chirality, i.e. the shape is not identical to its mirror image in left and right handed microscopes images viewed from either the top or the bottom. Therefore, a method is needed to determine which wells go with which blocks without presupposing a particular viewing direction. The three corners of the block that are not the start well have a unique orientation that points into the center of the block. Since there are two such orientations (e.g: well 602 and 603), the two orientations can be used to represent a binary 1 (well 602) and a binary 0 (well 603) in order to encode additional information. In this example, there are different well patterns each with a slightly different dimension so as to accommodate variations in PDMS shrinkage caused by different curing temperatures. The three corners encode for 8 different values, 0 through 7.

FIG. 10 shows a block encoding the three values: column 3, row 4 and pattern 5. The block is first located in a microscope's field of view by finding nonsymetrical well 601 which is designed to have the shape of a home-plate in baseball. Following four wells in the direction of well 601, well 602 defines the chirality of the block, in this case to the left. Wells 603 and 604 confirm this chirality. In addition, starting from the high bit, wells 604, 603 and 602 encode for the binary number 101 which, expressed in decimal, is the well pattern 5.

The column code starts with high bit 606 and ends with low bit 605: 000011, or column 3. The row code starts with high bit 608 and ends with low bit 607: 000100, or row 4.

This is an illustrative example only. The shapes can easily vary to accommodate different designs and materials, as well as the number of wells per block, the sizes and relative arrangements.

Insofar as the description above and the accompanying drawings disclose any additional subject matter that is not within the scope of the claims below, the inventions are not dedicated to the public and the right to file one or more applications to claim additional inventions is reserved.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A method of obtaining antigen binding and nucleic acid sequence information about antibodies produced from a plurality of isolated antibody producing cells, comprising the steps of:
placing a plurality of individual antibody producing cells in a plurality of individual wells;
contacting antibodies produced by the antibody producing cells in the wells with an antibody binding agent bound to a removable first top, to obtain surface bound antibodies, wherein the first removable top comprises regions relatable to the individual wells;
simultaneously determining binding information relating to binding of the antibodies bound to the first removable top to a known antigen and associating the binding information to a particular region of the first removable top and an individual well;
lysing the antibody-producing cells in the wells;
hybridizing mRNAs from the lysed antibody-producing cells with oligonucleotide probes comprising 1) tags, and 2) antibody light or heavy chain nucleic acid sequences that selectively bind to mRNAs that encode antibodies, wherein the oligonucleotide probes are bound to a second removable top, wherein the second removable top comprises regions relatable to the individual wells, and wherein the tags in each region are different;
converting the mRNAs hybridized to the second removable top into cDNAs which comprise the tags specific to the regions on the second surface;
releasing the tagged cDNAs from the second top;
pooling the tagged cDNAs;
sequencing the tagged cDNAs; and
utilizing the tags to associate the cDNA sequences to a particular well, which associates the cDNA sequences with binding information about the antibody produced by the antibody-producing cells in the wells.

2. The method of claim 1, further comprising: identifying a cDNA sequence corresponding to an antibody of interest and engineering a cell to operatively incorporate the cDNA to produce the antibody of interest.

3. The method of claim 1, wherein 1,000 or more individual antibody producing cells are placed in a corresponding number of individual wells of a well tray having a well density of 100 or more wells per cm$^2$ and the mRNA hybridized is mRNA that codes for a light and heavy chain of the antibody.

4. The method of claim 3, wherein 10,000 or more individual antibody producing cells of a well tray with a well density of 1,000 wells or more per cm$^2$ are placed in a corresponding number of individual wells.

5. The method of claim 4, wherein 100,000 or more individual antibody producing cells are placed in a corresponding number of individual wells.

6. The method of claim 3, wherein the wells are fabricated at a density of 1,000 or more wells per cm$^2$.

7. The method of claim 1, the method further comprising: after the contacting step, repeating the contacting step with a third removable top comprising a second antibody binding agent to bind antibodies produced by the antibody-producing cells.

8. The method in claim 1, wherein the ratio of the number of wells containing two or more cells divided by the number of wells containing a single cell is less than 1:5.

9. The method of claim 1, wherein the sequencing is accomplished by ultra-high throughput DNA sequencing technology.

10. A method of obtaining information from an isolated cell of interest, comprising the steps of:
placing a plurality of individual cells in a plurality of individual wells, wherein the cells produce antibodies;
contacting antibodies in the wells with antibody binding agents bound to a first a removable first top comprised of addressed regions, the address of the regions being relatable to the individual wells;
determining binding information of the antibodies bound to the first removable top to a known antigen;
associating the binding information of the antibodies bound to the first removable top with the wells from which the antibodies were obtained;
lysing the cells in the wells;
hybridizing nucleic acids from the lysed cells with oligonucleotide probes comprising 1) tags, and 2) antibody light or heavy chain nucleic acid sequences that selectively bind to nucleic acids from the lysed cells that encode antibodies, wherein the oligonucleotide probes are bound to a second removable top, wherein the second removable top comprises regions relatable to the individual wells, and wherein the tags in each region are different;
converting the nucleic acids from the lysed cells that have hybridized to the second removable top into copies of nucleic acids comprising the tags;
releasing the tagged copied nucleic acids from the second top;
pooling the copied nucleic acids;
obtaining nucleotide sequence information from the copied nucleic acids via ultra-high throughput sequencing; and
relating the nucleotide sequence information from the copied nucleic acids to the binding information from the bound antibodies produced by the antibody-producing cells in the wells.

11. The method of claim 10, further comprising: identifying a copied nucleic acid sequence corresponding to an antibody of interest and engineering a cell with the copied nucleic acid to produce an antibody.

12. The method of claim 10, wherein the oligonucleotide probes encode light and heavy chains of the antibodies.

13. A method of obtaining information from isolated cells of interest, comprising the steps of:
placing a plurality of individual cells in a plurality of individual wells, wherein the cells produce antibodies;
contacting antibodies in the wells with a protein bound to a first surface where the protein binds antibodies in the wells and where the first surface comprises address regions where the addresses are relatable to the individual wells;
determining binding information of the antibodies bound to the first surface to a known antigen;
associating the binding information of the antibodies bound to the first surface to wells from which the antibodies were obtained;
lysing the cells in the plurality of wells to obtain nucleic acid;
hybridizing nucleic acids from the lysed cells with oligonucleotide probes comprising 1) tags, and 2) antibody light or heavy chain nucleic acid sequences that selectively bind to nucleic acids from the lysed cells that encode antibodies, wherein the oligonucleotide probes are bound to a second surface, wherein the second surface comprises regions relatable to the individual wells, and wherein the tags in each region are different;

converting the nucleic acids from the lysed cells that have hybridized to the second removable top into copies of nucleic acids, wherein a tag is incorporated into the nucleic acid copies of the nucleic acids from the lysed cells, and wherein each tag is uniquely associated with a single well;

releasing the tagged copied nucleic acids from the second surface;

pooling the tagged copied nucleic acid copies from the plurality of wells;

sequencing the pooled tagged copied nucleic acid; and using the tags to associate the sequenced nucleic acids with wells, which associates nucleotide sequences with binding information from the antibodies.

14. The method of claim 13, wherein the protein bound to the surface is selected from the group consisting of Protein A, Protein G, Protein L, Protein A/G, and anti-IgG Fcγ-specific antibodies.

15. A method, comprising:

placing a plurality of antibody producing cells in a plurality of wells;

allowing the cells in the wells to exist under conditions such that the cells produce antibodies;

contacting the antibodies in the wells with a first surface comprising regions relatable to the wells, wherein the first surface comprises a first antibody binding agent;

determining binding information related to binding of the first antibody binding agent to the antibodies on the regions of the first surface;

contacting the antibodies in the wells with a second surface comprising regions relatable to the wells, wherein the second surface comprises a second antibody binding agent;

determining binding information related to binding of the second antibody binding agent to the antibodies on the regions of the second surface;

contacting the antibodies in the wells with a third surface comprising regions relatable to the wells, wherein the third surface comprises a third antibody binding agent;

determining binding information related to binding of the third antibody binding agent to antibodies on the regions of the third surface;

lysing the cells in the wells;

hybridizing the nucleic acids from the lysed cells with oligonucleotide probes comprising 1) tags, and 2) antibody light or heavy chain nucleic acid sequences that selectively bind to sequences that encode antibodies, wherein the oligonucleotide probes are bound to a fourth surface, wherein the fourth surface comprises regions relatable to the individual wells, and wherein the tags in each region are different;

converting the nucleic acids from the lysed cells that have hybridized to the fourth removable top into copies of nucleic acids, wherein a tag is incorporated into the copies of nucleic acids from the lysed cells, and wherein each tag is uniquely associated with a single well;

releasing the tagged copied nucleic acids from the fourth surface;

pooling the tagged copied nucleic acids from the plurality of wells;

sequencing the pooled tagged copied nucleic acids; and using the tags to associate the sequenced nucleic acids with wells, which associates nucleotide sequences with binding information from the antibodies.

16. The method of claim 15, wherein 10,000 or more wells are present on a tray at a density of 1,000 or more wells per $cm^2$.

17. The method of claim 1, wherein the oligonucleotide probes encode light and heavy chains of the antibodies.

18. The method of claim 13, wherein the oligonucleotide probes encode light and heavy chains of the antibodies.

19. The method of claim 15, wherein the oligonucleotide probes encode light and heavy chains of the antibodies.

* * * * *

SEQUENCE LISTING

```
<160> NUMBER OF SEQ ID NOS: 2

<210> SEQ ID NO 1
<211> LENGTH: 74
<212> TYPE: DNA
<213> ORGANISM: Mus musculus
<220> FEATURE:
<221> NAME/KEY: misc_difference
<222> LOCATION: (34)...(47)
<223> OTHER INFORMATION: n = A,T,C or G
<220> FEATURE:
<221> NAME/KEY: misc_difference
<222> LOCATION: 68
<223> OTHER INFORMATION: n = i

<400> SEQUENCE: 1
aaaaaactcg aggccttgcc agcccgctca gatnnnnnnn nnnnnnncag gggccagtgg      60
atagactnga tggg                                                       74

<210> SEQ ID NO 2
<211> LENGTH: 85
<212> TYPE: DNA
<213> ORGANISM: mus musculus
<220> FEATURE:
<221> NAME/KEY: misc_difference
<222> LOCATION: (34)...(47)
<223> OTHER INFORMATION: n = A,T,C or G

<400> SEQUENCE: 2
aaaaaactcg aggcctccct cgcgccatca gatnnnnnnn nnnnnnnctc cagatgttaa      60
ctgctcactg gatggtggga agatg                                           85
```